US012350420B2

(12) United States Patent
Franke et al.

(10) Patent No.: US 12,350,420 B2
(45) Date of Patent: Jul. 8, 2025

(54) FLUID DISPENSING DEVICE

(71) Applicant: Sanofi, Paris (FR)

(72) Inventors: Beate Franke, Rankfurt am Main (DE); Matthias Rau, Rüsselsheim (DE)

(73) Assignee: Sanofi, Paris (FR)

( * ) Notice: Subject to any disclaimer, the term of this patent is extended or adjusted under 35 U.S.C. 154(b) by 954 days.

(21) Appl. No.: 17/420,877

(22) PCT Filed: Jan. 7, 2020

(86) PCT No.: PCT/EP2020/050162
§ 371 (c)(1),
(2) Date: Jul. 6, 2021

(87) PCT Pub. No.: WO2020/144152
PCT Pub. Date: Jul. 16, 2020

(65) Prior Publication Data
US 2022/0080134 A1  Mar. 17, 2022

(30) Foreign Application Priority Data
Jan. 8, 2019  (EP) .................................... 19305020

(51) Int. Cl.
*A61M 11/00*  (2006.01)
(52) U.S. Cl.
CPC ..... *A61M 11/007* (2014.02); *A61M 2205/276* (2013.01)
(58) Field of Classification Search
CPC .............. A61M 15/08; A61M 15/0065; A61M 15/0025; A61M 15/0026;
(Continued)

(56) References Cited

U.S. PATENT DOCUMENTS 6,173,868 B1 * 1/2001 DeJonge ........... A61M 15/0026
222/321.6
6,261,274 B1 7/2001 Arghyris et al.
(Continued)

FOREIGN PATENT DOCUMENTS

CN    1203533    12/1998
CN    1360523    7/2002
(Continued)

OTHER PUBLICATIONS

International Preliminary Report on Patentability in International Appln. No. PCT/EP2020/050162, dated Jun. 16, 2021, 9 pages.
(Continued)

*Primary Examiner* — Rachel T Sippel
*Assistant Examiner* — Gwynneth L Howell
(74) *Attorney, Agent, or Firm* — Bond, Schoeneck & King, PLLC

(57) ABSTRACT

The disclosure relates to a fluid dispensing device including: a housing including an orifice and configured to accommodate a portion of a spray delivery device including an outlet, a protective cap configured to accommodate the outlet of the spray delivery device and including a cap portion, wherein the protective cap is configured for fitting to the housing so that the cap portion covers the orifice, a biasing member transferable between a pre-loaded state and an unloaded state and configured to store energy in the pre-loaded state to produce a discharge of the spray delivery device, a releasable interlock configured to retain the biasing member in the pre-loaded state, a trigger engaged with the interlock and configured to release the interlock when actuated, wherein release of the energy stored in the pre-loaded biasing member is prevented as long as the cap portion covers the orifice.

17 Claims, 24 Drawing Sheets

(58) Field of Classification Search
CPC .......... A61M 2205/276; A61M 11/007; A61M 15/085; A61M 15/009; A61M 11/00; A61M 11/006; A61M 11/06–08; B05B 11/00; B05B 11/1059; B05B 11/0027; B05B 11/0038; B05B 11/1015; B05B 11/1053; B05B 11/1091; B05B 11/1092; B05B 11/0032

See application file for complete search history.

(56) References Cited

U.S. PATENT DOCUMENTS

| | | | |
|---|---|---|---|
| 6,288,352 B1 | 9/2001 | Fukui et al. | |
| 6,708,846 B1 | 3/2004 | Fuchs et al. | |
| 7,302,948 B2* | 12/2007 | Anderson | B05B 11/0032 128/200.22 |
| 7,757,901 B2* | 7/2010 | Welp | B05B 11/0032 222/323 |
| 9,475,074 B2* | 10/2016 | Auerbach | B05B 11/1091 |
| 2004/0011822 A1* | 1/2004 | Jennings | A61M 15/0025 222/321.8 |
| 2006/0191959 A1* | 8/2006 | Davies | B05B 11/1056 222/402.15 |
| 2008/0116223 A1 | 5/2008 | Stradella | |
| 2008/0210228 A1 | 9/2008 | Corbacho | |
| 2011/0066136 A1* | 3/2011 | Moller | A61M 11/08 604/514 |

FOREIGN PATENT DOCUMENTS

| | | |
|---|---|---|
| CN | 101600469 | 12/2009 |
| CN | 103889587 | 6/2014 |
| CN | 105025954 A | 11/2015 |
| DE | 29908923 | 7/2000 |
| FR | 2682305 | 4/1993 |
| GB | 2489216 | 9/2012 |
| JP | 2001-516236 A | 9/2001 |
| WO | WO 1997/020590 | 6/1997 |
| WO | WO 2001/003851 | 1/2001 |
| WO | WO 2002/030503 | 4/2002 |
| WO | WO 2008/077623 | 7/2008 |
| WO | WO 2013/054076 | 4/2013 |
| WO | WO 2014/131858 A1 | 9/2014 |

OTHER PUBLICATIONS

International Search Report and Written Opinion in International Appln. No. PCT/EP2020/050162, dated Apr. 14, 2020, 11 pages.

* cited by examiner

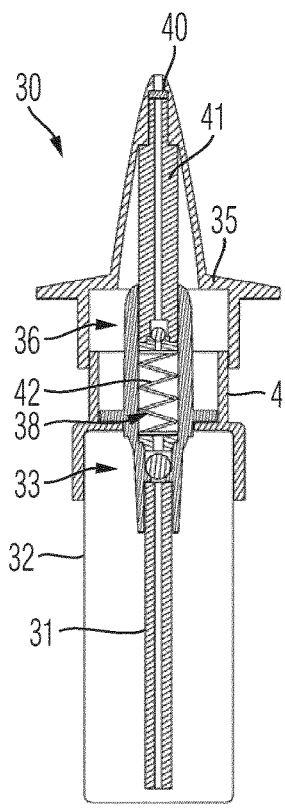
Fig. 38
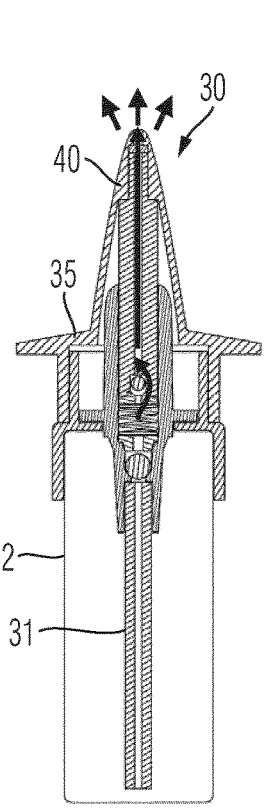
Fig. 39
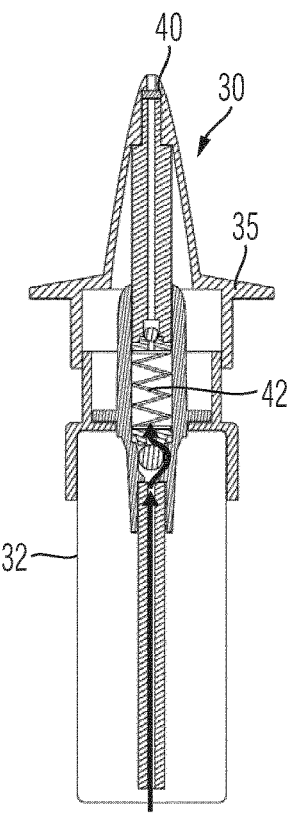
Fig. 40
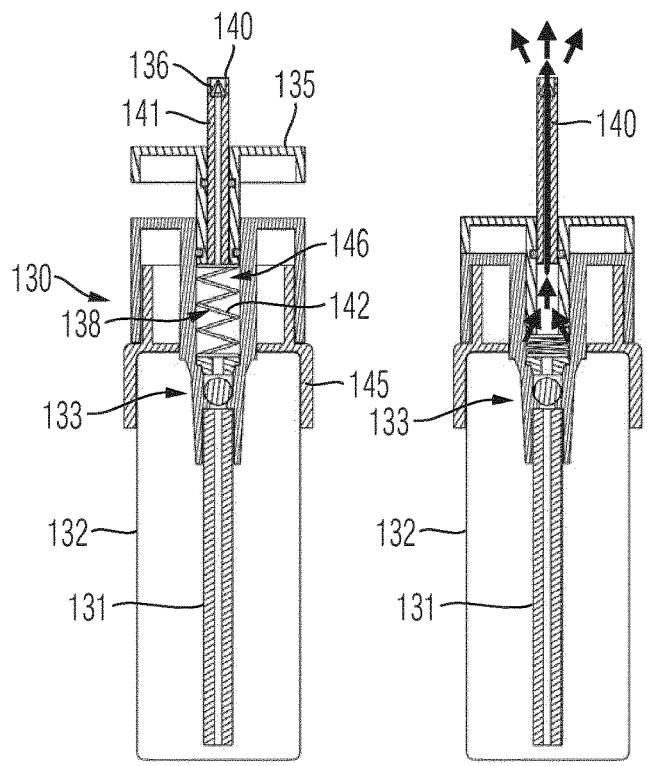
Fig. 41
Fig. 42
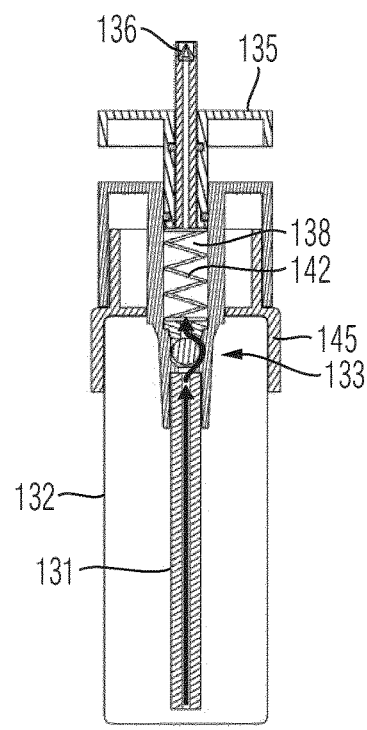
Fig. 43

FLUID DISPENSING DEVICE

CROSS REFERENCE TO RELATED APPLICATIONS

The present application is the national stage entry of International Patent Application No. PCT/EP2020/050162, filed on Jan. 7, 2020, and claims priority to Application No. EP 19305020.0, filed on Jan. 8, 2019, the entire disclosures of which are incorporated herein by reference.

TECHNICAL FIELD

The present disclosure relates to the field of fluid dispensing devices and to fluid dispensing devices configured as nasal inhalers. The disclosure further relates to spray devices configured to dispense a fluid or a liquid substance by way of spraying or atomizing.

BACKGROUND

Fluid dispensing devices operable to atomize a liquid substance are as such known. Such devices typically comprise a nozzle or an orifice. Upon application of a force by a user to an actuation lever or a button the fluid is dispensed via the nozzle or orifice. Such devices may be arranged to dispense a single dose or such devices may be equipped with a container providing a reservoir for the fluid thus allowing and supporting the dispensing of several doses.

The efficacy of a dispensing action is dependent upon the manner in which the device is actuated by a user. Dispensing of the fluid is less efficient when an actuation force applied by a user is comparatively low or if the user-induced action is rather slow.

There have been described so called pre-loaded or pre-biased fluid dispensing devices, wherein a force required for a dispensing procedure is provided by a biasing member. Such pre-loaded fluid dispensing devices may be configured to remain in a pre-loaded state for a comparatively long time. With a pre-loaded fluid dispensing device there is always a certain risk of an uncontrolled, premature or inadvertent dispensing of a dose of the fluid.

It is therefore desirable to provide an improved fluid dispensing device of pre-loadable type being less susceptible to an uncontrolled, premature or inadvertent dispensing action. The fluid dispensing device should provide a rather simple, effective and intuitive approach to prevent an uncontrolled, premature or inadvertent dispensing action of a pre-loaded fluid dispensing device. The intended prevention of uncontrolled, premature or inadvertent dispensing of the fluid should be easily implementable. The respective prevention mechanism should be reliable, robust and durable over the entire lifetime of the fluid dispensing device.

SUMMARY

In one aspect there is provided a fluid dispensing device. The fluid dispensing device comprises a housing. The housing comprises an orifice. The housing of the fluid dispensing device is further configured to accommodate at least a portion of a spray delivery device. Typically, the spray delivery device comprises an outlet through which a fluid stored in the spray delivery device can be discharged, e.g. by way of a spraying.

When appropriately arranged inside the housing or when attached to the housing the outlet of the spray delivery device may cooperate with the orifice of the fluid dispensing device.

The fluid dispensing device further comprises a protective cap defining an interior space, e.g., in the form of a hollow interior. The protective cap is configured to accommodate the outlet of the spray delivery device. The protective cap further comprises a dedicated cap portion. The protective cap is further configured for fitting to the housing at least in a closing position relative to the housing. In the closing position the cap portion of the protective cap covers the orifice of the housing of the fluid dispensing device.

A dispensing device further comprises a mechanical biasing member that is reversibly transferrable between a pre-loaded state and an unloaded state. The biasing member is configured to store mechanical energy in the preloaded state. The mechanical energy storable in the mechanical biasing member is effective to produce a spray discharge of the spray delivery device. In other words, the biasing member is operable to induce spray discharge action of the spray delivery device when appropriately assembled to the housing of the fluid dispensing device.

The fluid dispensing device further comprises a releasable interlock configured or operable to retain the biasing member in the pre-loaded state. The fluid dispensing device further comprises a manually actuatable trigger operably engageable with the interlock or operably engaged with the interlock. The trigger is operable to release the interlock when actuated.

A trigger-actuation induced release of the interlock releases the biasing member from the pre-loaded state and allows the biasing member to transfer into the unloaded state, thus releasing mechanical energy to induce or to effectuate a spray discharge of the spray delivery device.

With the fluid dispensing device, release of the mechanical energy stored in the pre-loaded mechanical biasing member through actuation of the trigger is prevented as long as the cap portion of the protective cap covers the orifice. In other words, release of the energy stored in the mechanical energy reservoir by actuation of the trigger is prevented unless the cap is removed from covering the orifice.

In situations, in which the protective cap is moved relative to the housing into a state or configuration, in which the cap portion no longer covers the orifice, it is no longer an obstacle to the delivery of a spray discharge or spray jet emanating from the outlet of the spray delivery device.

By preventing release of the mechanical energy stored in the pre-loaded mechanical biasing member as long as the cap portion covers the orifice it can be provided, that the fluid or the spray discharge is not inadvertently wasted, e.g., by impinging to an inside face of the protective cap.

Typically, the protective cap is displaceable between a closing position and an opening position. In the open position or before reaching the opening position the cap portion many longer cover or obstruct the orifice.

In a further example, the protective cap is mechanically engaged with at least one of the interlock and the trigger when in the closing position. Typically, when in the closing position, the protective cap or at least the cap portion end thereof at least partially covers the orifice of the fluid dispensing device. When in the opening position, the orifice is uncovered and is thus configured to dispense the fluid, e.g., by way of spraying. When in the closing position and when covering the orifice the protective cap effectively blocks and hinders a dispensing action of the fluid dispensing device, which dispensing action may be initiated and/or effectuated by the mechanical biasing member.

Typically, the mechanical biasing member is either directly or indirectly operably engaged with the spray delivery device. When the biasing member is subject to a transfer from the pre-load, hence biased state, into the unloaded, hence unbiased state, the biasing member is operable to induce a movement of the spray delivery device or a component thereof relative to the housing of the fluid dispensing device in order to induce or to effectuate a spray delivery through the outlet of the spray delivery device.

With some examples, the mechanical biasing member is configured to induce or to effectuate a movement of a first part of the spray delivery device relative to a second part of the spray delivery device. Here, a relative movement of the first part of the spray delivery device relative to the second part of the spray delivery device leads to a spray discharge through the outlet of the spray delivery device. With some examples, the spray delivery device comprises the outlet and a container. Here, the outlet may represent the first part of the spray delivery device and the container may represent the second part of the spray delivery device.

With other examples, the spray delivery device comprises a movable part and a container, wherein the movable part represents the first part of the spray delivery device and wherein the container represents the second part of the spray delivery device. The movable part and the container are movable relative to each other. Here, the outlet may be rigidly, i.e., immovably connected to one of the movable part and the container.

With some examples, as long as the protective cap is in the closing position, actuation of the trigger to release the interlock and/or to release the biasing member is effectively blocked or hindered. Moreover, as long as the protective cap is in the closing position, a manipulation of the interlock can be effectively blocked and hindered. Insofar, the interlock persists in an interlock configuration, in which the mechanical biasing member is retained and/or fixed in the pre-loaded state.

In effect, as long as the protective cap is in the closing position a dispensing operation of the fluid dispensing device is effectively blocked. An uncontrolled, premature or inadvertent dispensing of the fluid can be hence effectively prevented as long as the protective cap is in the closing position and as long as the protective cap is in a predetermined position relative to the housing.

With some examples, the mechanical biasing member is implemented as a spring element. It is transferrable into the pre-loaded state against a restoring action of the spring element. When the biasing member transfers from the pre-loaded state into the unloaded state, a spring force is released and the mechanical biasing member is operable to induce or to effectuate a discharge operation of the spray delivery device, e.g. by applying a respective spring force to the spray delivery device, the housing, the container and/or to the moveable part of the spray delivery device.

In a further example the protective cap is at least one of detachably connectable to the housing, pivotally connected to the housing, and slidably connected to the housing. Transferring of the protective cap from the closing position into the opening position may include detaching the protective cap from the housing to uncover and to reveal the nozzle.

Pivoting the cap relative to the housing includes revealing or providing access to the orifice or sliding the protective cap along or relative to the housing into a configuration in which the orifice for the outlet of the spray delivery device is unobstructed and hence revealed. Typically, the housing and the protective cap comprise at least one fastener configured to retain the protective cap in the closing position. The fastener may comprise one of a flip joint, a snap fit engagement or a clamp joint. Depending on the specific implementation of a joint or engagement between the housing and the protective cap, the housing and the protective cap comprise mutually corresponding and inter-engaging fastening features. For instance, when the fastener is implemented as a clip joint, the housing comprises at least one clip feature configured to cooperate with a counter clip feature of the protective cap. When implemented as a snap fit engagement, the housing comprises at least one snap feature configured to engage with a correspondingly or complementary-shaped counter snap feature of the protective cap. In this way, a releasable and/or detachable engagement between the housing and the protective cap can be provided.

According to a further example, when in the closing position the protective cap is operable or configured to block the trigger of the fluid dispensing device. For this, the protective cap may comprise a blocking portion to engage or to cooperate with the trigger. Typically, the blocking portion of the protective cap at least partially overlaps or engages with the trigger when the cap is in the closing position, i.e., when the cap is assembled or attached to the housing. In this way, the cap, i.e., its blocking portion hinders activation, e.g., a depression of the trigger relative to the housing. The fluid dispensing mechanism is hence blocked and is thus inoperable to dispense a dose of the fluid as long as the protective cap is and remains in the closing position.

In a further example the protective cap covers the trigger when in the closing position. Here, the trigger is arranged close to a portion of the housing that can be covered by the protective cap when in the closing position. As long as the protective cap is in the closing position at least a portion thereof covers and/or obstructs the trigger. In this way, the trigger is inaccessible for a user and as long as the protective cap is mounted on the fluid dispensing device or on its housing the trigger simply cannot be actuated for dispensing of a dose of the fluid.

With some examples the blocking portion of the protective cap represents an extension of a dome-shaped sidewall of the protective cap, which at least partially covers the trigger when the protective cap is attached to the housing, i.e. when the protective cap is in the closing position. With some examples, the trigger is arranged recessed compared to an outer surface of the housing of the fluid dispensing device or the trigger is at least arranged flush with the housing. In both cases, the trigger, e.g., implemented as a button or as a slider, does not protrude from the outer circumference of the housing.

Covering of the trigger by the protective cap has no influence on the trigger. Typically, the protective cap or a portion thereof may extend entirely over the trigger. The cap may abut with a wall portion of the housing confining the trigger arranged in a recessed configuration compared to the outer surface of the respective wall portion of the housing. In this way, the portion of the protective cap effectively covering the trigger can be in abutment with the housing portion. Any excessive force effect eventually applied on the protective cap in the region of the trigger located underneath can be counteracted by the respective wall portion of the housing and is ineffective to depress or to actuate the trigger located underneath or below the protective cap.

Moreover, covering the trigger by the protective cap is also of further benefit for that the user does not even know where the trigger is actually located as long as the cap is mounted on the fluid dispensing device. Any misuse of the device or inadvertent and premature as well as uncontrolled actuation of the trigger can be thus effectively prevented and avoided.

With a further example and when in the closing position, the protective cap is operable to block a release of the interlock. In particular, the protective cap or a portion thereof is operable and/or configured to hinder or to block a movement of the interlock and to keep the interlock in a locked configuration, in which the mechanical biasing member is retained in the pre-loaded state.

For this, the protective cap or a portion thereof may be operably engageable with the interlock when the protective cap is in the closing position. The protective cap may be operably engaged exclusively with the interlock. It may be operably engaged with both, the interlock as well as with the trigger when the protective cap is in the closing position. Alternatively, the protective cap or a portion thereof may be operably engageable with the trigger to prevent actuation thereof. Here, the protective cap or a portion thereof may be exclusively configured to disable an actuation of the trigger only or to disable both, actuation of the trigger as well as a release of the interlock. In order to prevent an uncontrolled, a premature or an inadvertent dispensing action of the fluid dispensing device it may be sufficient when the protective cap is only engaged with one of the interlock and the trigger. In a further example, the protective cap or a portion thereof may be operably engageable with both the interlock and the trigger simultaneously when in the closing position or when approaching the closing position.

With another example, the protective cap is transferable into the opening position relative to the housing. Moreover, the protective cap is operable to actuate the trigger as the protective cap approaches or reaches the opening position. Here, it is of particular benefit when the protective cap reaches a well-defined opening position relative to the housing. This can be achieved, e.g., by a persistent connection of the protective cap and the housing, e.g., when the protective cap is either pivotally or slidably connected to the housing.

An outside facing portion of the protective cap may engage with the trigger of the fluid dispensing device accessible from outside the dispensing device when the protective cap reaches or approaches the opening position. In this way, a quasi-automated actuation of the spray delivery can be initiated and effectuated by transferring the protective cap from the closing position into the opening position.

With another example, the trigger may be located inside the housing and may be inaccessible from outside the housing. The trigger may be then exclusively operably engageable with the protective cap. For this, the protective cap may comprise a cam configured and/or operable to actuate the trigger when reaching or approaching the opening position.

With another example of the fluid dispensing device, the manually actuatable trigger is located in a recess or in a recessed portion of the housing. It may be also located inside the housing. The trigger is recessed with regard to an outside surface of the housing. It does not protrude from the housing. Typically, a user-actuatable surface or section of the trigger is located inside the recess or recessed portion and is located at a predefined non-zero distance from an outer edge of the recess or recessed portion. Typically, the trigger is accessible from outside the housing. The recess or recessed portion of the housing is comparatively small in cross-section. The cross-section of the recess or recessed portion, in which the trigger is located, is typically smaller than the diameter or cross-section of a human finger. Insofar, a specific tool is required to enter the recessed portion of the housing and to actuate the trigger. In this way, unintentional actuation or depression of the trigger is effectively prevented.

With a further example the protective cap comprises a protrusion extending outwardly from an outside surface of the protective cap. The protrusion is sized and shaped to enter the recessed portion of the housing from outside the housing. The protrusion is further configured to engage or to depress the manually actuatable trigger. When the protective cap is pivotally attached to the housing by a hinge including a hinge axis, a radial distance between the protrusion and the hinge axis may be somewhat equal or equivalent to a radial distance between the recessed portion of the housing and the hinge axis. In this way, the hinged connection of the protective cap to the housing provides a forced guidance for the protective cap and reduces the available degrees of freedom of movement of the protective cap. In this way it can be guaranteed that when approaching or reaching the opening position the protrusion of the protective cap engages with the manually actuatable trigger.

With a further example the interlock comprises a slider slidably guided along a first direction of movement by a guiding structure of the housing. In this way, the interlock is slidably displaceable relative to the housing between an interlock position and a release position. In the interlock position the interlock is mechanically engaged with at least one of the spray delivery device and a mechanical coupler configured to receive or to accommodate the spray delivery device. In the release position or release configuration the slider allows and supports a movement of the spray delivery device or at least a portion thereof, which movement is effective to produce the spray discharge of the spray delivery device.

With a further example the interlock is displaceable from the interlock position or interlock configuration into or towards the release position or release configuration against the action of a return spring. In this way the interlock and/or the slider of the interlock is biased towards the interlock position or interlocked configuration thus providing a self-actuated activation of the interlock when the mechanical biasing member is transferred into the pre-loaded state.

With a further example, the fluid dispensing device further comprises a mechanical coupler engaged with the mechanical biasing member. The mechanical coupler is displaceable relative to the housing at least into a preload position for transferring the biasing member into the pre-loaded state. Typically, the mechanical coupler is displaceable relative to the housing between the preload position and an unload position. The preload position and the unload position may also be denoted as biased position or unbiased position, respectively. Moreover, one of the mechanical coupler and the biasing member of the fluid dispensing device is operably engageable or is operably engaged with the spray delivery device.

Typically, the mechanical biasing member comprises a first end and an oppositely located second end. One end of the mechanical biasing member is in mechanical engagement or abutment with at least one of the housing and the mechanical coupler. The opposite end, hence the second end of the biasing member is typically connected to or in abutment with one of the mechanical coupler and one of the container or moveable part of the spray delivery device.

There are examples, wherein the mechanical biasing member is arranged between the housing and the mechanical coupler. Here, the biasing member is configured to induce a relative displacement between the mechanical coupler and the housing of the fluid dispensing device. Here, the mechanical coupler is displaceable relative to the housing into the preload position against the action of the biasing member. The mechanical coupler is then displaceable from the preload position into an unload position under the action of a relaxing biasing member. Here, one end of the biasing member is connected to or is in abutment with the mechanical coupler and the other end of the biasing member is connected to or is in abutment with the housing of the fluid dispensing device.

With another example the mechanical biasing member is arranged between the spray delivery device or one of the first and second parts thereof and one of the housing and the mechanical coupler of the fluid dispensing device. In this way, the mechanical coupler is operable to induce a displacement of the spray delivery or one of its first and second parts relative to at least one of the housing and the mechanical coupler of the fluid dispensing device. One end of the biasing member is connected to or is in abutment with the container of the spray delivery device and an opposite end of the biasing member is connected to or is in abutment with one of the housing and the mechanical coupler of the fluid dispensing device.

When the mechanical biasing member is operable to induce a displacement of one of the first and second parts of the spray delivery device relative to the housing, the other one of the first and second parts of the spray delivery device is typically fixed to the housing. In particular, the outlet of the spray delivery device may be fixed to the housing and/or to the orifice of the dispensing device.

With another example the mechanical biasing member is arranged between one of the first and second parts of the spray delivery device, e.g., the movable part, and one of the housing and the mechanical coupler. In this way, the mechanical coupler is operable to induce a biasing of the biasing member. Here, one end of the mechanical biasing member is connected to or is in abutment with the movable part of the spray delivery device and an opposite end of the mechanical biasing member is connected to or is in abutment with one of the housing and the mechanical coupler of the fluid dispensing device. Here and when the mechanical biasing member is operable to induce a displacement of the moveable part of the spray delivery device relative to the housing of the fluid dispensing device one of the first and second parts of the spray delivery device, e.g., the container of the spray delivery device may be fixed inside or to the housing of the fluid dispensing device.

With a further example of the spray delivery device the mechanical coupler is operably engaged with the container of the spray delivery device. Here, the biasing member is typically engaged with the mechanical coupler and the housing of the fluid dispensing device. The mechanical coupler is hence displaceable relative to the housing against the action of the biasing member. The mechanical coupler can be fixed to the container or may be in abutment with the container of the spray delivery device when the spray delivery device is assembled inside the housing.

The moveable part of the spray delivery device may be fixed to the housing of the fluid dispensing device. Insofar, the transfer of the biasing member from the pre-loaded state into the unloaded state leads to a respective displacement of the mechanical coupler and of the container relative to the housing of the fluid dispensing device and hence relative to the moveable part, thus leading to a dispensing of a spray dose from the spray delivery device and hence from and through the nozzle of the fluid dispensing device.

With another example the mechanical coupler is operably engageable with the moveable part. When the spray delivery device is assembled inside the housing of the fluid dispensing device the mechanical coupler may be either connected to the moveable part and/or may be in abutment with the moveable part. Here, the container of the spray delivery device may be fixed inside the housing of the fluid dispensing device. The biasing member may be arranged between the housing and the mechanical coupler. Hence, a transfer of the biasing member from the pre-loaded state into the unloaded state leads to a respective displacement of the mechanical coupler and of the moveable part relative to the housing.

Since the container is fixed to the housing the movement of the mechanical coupler and the moveable part relative to the housing leads to a displacement of the moveable part relative to the container, thus leading to a respective dispensing of a dose of the fluid from the spray delivery device and hence from and through the nozzle of the housing.

With another example it is the biasing member that is operably engaged with one of the container and the moveable part. Here, one end of the biasing member is connected or is in abutment with one of the container and the moveable part of the spray delivery device whereas an opposite end of the biasing member is connected to or is in abutment with the mechanical coupler. Here, a displacement of the mechanical coupler into the preload position relative to the housing may lead to a transfer of the mechanical biasing member into the pre-loaded state.

A transfer of a biasing member from the pre-loaded state into the unloaded state may be accompanied or may result in a displacement of at least one of the container and the moveable part relative to the mechanical coupler and/or relative to the housing of the fluid dispensing device. Here, during the pre-loading of the biasing member that end of the biasing member connected to or in abutment with at least one of the container and the moveable part remains stationary, whereas the opposite end of the biasing member engaged with the mechanical coupler, i.e. connected to or in abutment with the mechanical coupler is subject to a displacement as the mechanical coupler is transferred into the preload position.

During and for dispensing of the dose the mechanical coupler may remain in the preload position. Only that end of the biasing member in engagement with at least one of the container and the moveable part may be subject to a return movement upon release of the interlock. Here and in the same way as described above the biasing member is configured and operable to induce a displacement of the moveable part of the spray delivery device relative to the container of the spray delivery device, thus leading to a dispensing of a dose of the fluid from the outlet of the spray delivery device and e.g. even through the orifice of the fluid dispensing device.

In examples, wherein one of the mechanical coupler and the biasing member is operably engaged, i.e., connected to or in abutment with the container of the spray delivery device, the moveable part of the spray delivery device may be fixed inside the housing of the fluid dispensing device when the spray delivery device is assembled inside said housing. When the mechanical coupler or the biasing member is operably engaged with the moveable part of the spray delivery device the container of the spray delivery device may be fixed inside the housing of the fluid dispensing device when the fluid dispensing device is assembled therein.

Typically and with nearly all examples of the fluid dispensing device that one of the container and the moveable part of the spray delivery device that is operably engaged with the mechanical coupler or the biasing member of the fluid dispensing device is moveable relative to the housing of the fluid dispensing device when the spray delivery device is assembled inside or fixed to the housing whereas the other one of the container and the moveable part is fixed inside or to the housing.

According to another example the protective cap is operably engageable with the mechanical coupler and the protective cap is operable to displace the mechanical coupler into the preload position when the protective cap approaches the closing position. Here, the movement of the protective cap from the opening position into the closing position causes a displacement of the mechanical coupler relative to at least one of the housing and the biasing member. In this way the biasing member is transferrable from the unloaded state into the pre-loaded state simply by moving the protective cap from the opening position into the closing position.

During a respective closing movement of the protective cap relative to the housing the protective cap may operably and/or mechanically engage with the mechanical coupler thus slaving the mechanical coupler into a respective movement direction of the cap as the protective cap is moved towards and into the closing position. This cap-induced displacement or movement of the mechanical coupler is sufficient to bring the mechanical coupler into the preload position, in which the interlock is either manually or automatically activated so as to retain at least one of the biasing member and the mechanical coupler in the pre-loaded state or preload position.

The mutual engagement of the protective cap with the mechanical coupler is of particular benefit for a practical and user-friendly handling of the fluid dispensing device. So, after a dispensing procedure has been executed leaving the biasing member in the unloaded state the closing movement of the protective cap inherently and quasi-automatically leads to a movement and displacement of the mechanical coupler towards and into the preload position. This movement of the coupler is accompanied by the transfer of the biasing member from the unloaded state into the pre-loaded state. When arriving in the preload position the interlock is activated thus keeping the biasing member in the pre-loaded state until the trigger is actuated or depressed.

While the fluid dispensing device may be kept in a storage position with the protective cap mounted thereon its dispensing mechanism provided by the mechanical biasing member, the mechanical coupler, the interlock and the trigger and the housing is and remains pre-loaded. An uncontrolled, premature or inadvertent activation of the trigger and a respective release of the interlock is effectively prevented as long as the protective cap is in the closing position.

The mutual engagement of the protective cap with the mechanical coupler provides a rather automated and self-actuated biasing or pre-loading of the biasing member during and by a closing action of the protective cap. In this way, the user of the fluid dispensing device does not have to pre-load or to bias the dispensing mechanism manually or separately. Upon removal or opening of the protective cap the fluid dispensing device is ready to use.

In a further example the protective cap comprises a longitudinal extension extending into through the interior space. The interior space may comprise or form a hollow interior. The longitudinal extension may extend from a sidewall or from an end wall of the protective cap. It may protrude into or even through the interior space. The longitudinal extension is configured to reach through at least one of the orifice or through a through opening in an end face or sidewall of the housing when the protective cap approaches the closing position. In this way, the longitudinal extension, at least a free end thereof is allowed to enter the housing of the fluid dispensing device. In this way, the longitudinal extension and/or the protective cap may operably or mechanically engage with the mechanical coupler which is arranged inside the housing of the fluid dispensing device.

The longitudinal extension in cooperation with the through opening of the housing enables an arrangement of the mechanical coupler entirely inside the housing. Arranging of the mechanical coupler inside the housing provides an inherent protection against manual, inadvertent or inhibited manual operation or displacement of the mechanical coupler relative to the housing. In this way, patient safety can be further enhanced. Typically, the through opening is sized to exclusively receive the longitudinal extension of the protective cap. It is typically smaller in diameter or cross-section than a cross-section or diameter of, e.g., a finger or of a pen or pencil. In this way, any unauthorized manipulation or movement of the mechanical coupler from outside the housing can be effectively prevented.

With a further example the mechanical coupler comprises an abutment that is configured to engage with the longitudinal extension of the protective cap. The abutment is particularly configured to engage with a free end of the longitudinal extension, e.g., facing away from the hollow interior of the protective cap. Typically, the abutment of the mechanical coupler faces towards the through opening of the housing and hence towards the longitudinal extension as the longitudinal extension enters the housing through the through opening.

Typically, the abutment of the mechanical coupler and the through opening of the housing are arranged on a virtual line or path. This line or path typically extends or runs substantially parallel to the elongation of a guiding structure of the housing defining a displacement path for the biasing member. In this way, and when the longitudinal extension enters and reaches through the through opening and gets in abutment with the abutment of the mechanical coupler a further movement of the longitudinal extension along this virtual line or path leads to and induces a respective displacement of the mechanical coupler along a guiding structure of the housing until the mechanical coupler reaches the preload position.

The virtual line or path is geometrically adapted to the closing and opening movement of the protective cap relative to the housing. If the protective cap is to be placed onto the housing along a longitudinal sliding or longitudinal displacement motion the longitudinal extension may be of straight shape and may extend along or parallel to the moving direction of the protective cap relative to the housing during a closing motion of the protective cap. With other examples, wherein the protective cap is pivotally arranged to the housing and is hence subject to a swiveling or pivoting motion to arrive in the open and closing positions, respectively, the virtual line or path between the abutment of the mechanical coupler and the through opening of the housing may comprise an arched structure or may follow a circle.

In a further example the housing comprises a longitudinal guiding structure that is operable to guide the mechanical coupler. The mechanical coupler is displaceable between the preload position and an unload position along this longitudinal guiding structure. Typically, the mechanical coupler is displaceable along the longitudinal guiding structure from the unload position towards and into the preload position against the action of the biasing member.

When the mechanical coupler is operably engageable or when the mechanical coupler is operably engaged with the spray delivery device or with at least one of the first and second parts of the spray delivery device, the spray delivery device and/or one of the first and second parts thereof is displaceable along the longitudinal guiding structure. The longitudinal guiding structure of the housing provides a longitudinal guiding function of at least the mechanical coupler and at least one of the spray delivery device and/or one of the first and second part of the spray delivery device in order to induce a relative longitudinal motion between the moveable part and the container of the spray delivery device.

The longitudinal guiding structure may provide or define a displacement path at least for the mechanical coupler and at least one of the first and the second parts of the spray delivery device, which may be implemented as the container and the movable part of the spray delivery device. The displacement path may extend parallel to a moving direction of the protective cap along which the protective cap has to be displaced for transferring the protective cap from the opening state into the closing state. When the protective cap is pivotally arranged to the housing the mutual abutment of the longitudinal extension of the protective cap and the abutment of the mechanical coupler may compensate for any radial displacement of the longitudinal extension relative to the mechanical coupler during a closing movement of the protective cap.

According to a further example the interlock comprises an aperture sized to receive at least one of the mechanical coupler and the spray delivery device. With some examples the interlock comprises a slider and the slider comprises the aperture sized to receive at least one of the mechanical coupler and the spray delivery device. In the interlock position or interlock configuration the interlock is misaligned with regards to the position or dimension of the mechanical coupler and/or of the spray delivery device. Then, an edge of the aperture of the interlock is engaged with an abutment of the mechanical coupler. Here, the edge of the aperture serves as a counter abutment to engage with the abutment of the mechanical coupler.

A trigger-induced movement or deformation of the interlock serves to align the aperture of the interlock with the mechanical coupler so that the engagement or abutment between the abutment and the counter abutment is abrogated and the mechanical coupler and/or other spray delivery device are allowed to enter order to intersect the aperture of the interlock.

In a further example the interlock comprises a resiliently deformable oval shaped ring structure. When and as long as the interlock is in the interlock position or interlocked configuration the ring structure is of a first ellipticity. When resiliently deformed towards and/or into the release position or release configuration the ring structure is of a second ellipticity. The second ellipticity is less than the first ellipticity. In other words, the second ellipticity resembles more a circular structure than the first ellipticity. The differences between long and short axes of the ring structure in the first ellipticity is larger than with the ring structure in the second ellipticity.

In another example the interlock comprises a catch feature and a correspondingly-shaped snap feature. The trigger is operable to apply a release force onto the catch feature effective to bring the catch feature and the snap feature out of engagement. At least one of the catch feature and the snap feature is either resiliently deformable or is displaceable, i.e., moveable or pivotable against a restoring force such as to enable a release of the catch feature and the correspondingly or complementary-shaped snap feature. The catch feature and the snap feature are configured to mutually engage as soon as the mechanical coupler arrives in the preload position.

At least one of the catch feature and the snap feature is displaceable, pivotable or resiliently deformable against a restoring force that is effective to keep the catch feature and the snap feature in mutual engagement such as to activate the interlock and to retain the biasing member in the pre-loaded state. It is upon a user-induced and/or trigger-induced displacement of one of the catch feature and the snap feature relative to the other one of the snap feature and the catch feature to bring the snap feature and the catch feature out of engagement. The interlock is then released or deactivated and allows or supports a relaxing or unloading of the biasing member, which is effective to induce a relative movement between the container and the moveable part of the spray delivery device when the spray delivery device is assembled inside the fluid dispensing device.

In a further example one of the catch feature and the snap feature is provided on or is attached to the mechanical coupler. The other one of the catch feature and the snap feature is provided on or is attached to the housing. In this way and when approaching the preload position the interlock is operable to fit the mechanical coupler in the preload position relative to the housing. Upon release of the interlock the mechanical coupler may become subject to an oppositely directed movement under the effect of the relaxing or biasing member.

Here it is of particular benefit when the mechanical coupler is mechanically engaged with or is fixed to one of the first and second parts of the spray delivery device whereas the other one of the first and second parts of the spray delivery device is fixed to or in abutment with the housing of the dispensing device.

With another example one of the catch feature and the snap feature is provided on or is attached to the mechanical coupler and the other one of the catch feature and the snap feature is provided on or is attached to one of the first part and second part of the spray delivery device. Here, the container or the moveable part of the spray delivery device may remain stationary relative to the housing of the fluid dispensing device while the mechanical coupler is subject to a displacement relative to the housing during and for bringing the mechanical coupler into the preload position. Here, the at least one of the catch or snap feature provided on the mechanical coupler may engage with the complementary-shaped snap feature or catch feature provided on one of the container and the moveable part of the spray delivery device. Upon deactivation or release of the interlock one of the first part and second part of the spray delivery device will be allowed to become subject to a displacement relative to the mechanical coupler. During a dispensing action the mechanical coupler may remain stationary relative to the housing whereas at least one of the first part and the second part of the spray delivery device is subject to a displacement, typically along the guiding structure of the housing.

With this example the biasing member is typically arranged between the mechanical coupler and at least one of the first part and the second part of the spray delivery device, e.g., one of the container and the moveable part of the spray delivery device. Here, and by displacing the mechanical coupler from the unload position towards and into the preload position the biasing member is appropriately pre-loaded or biased. When arriving in the preload position the interlock provided between the mechanical coupler and one of the first part and the second part of the spray delivery device is activated thus keeping and locking the mechanical coupler in the preload position.

Upon activation of the trigger and a resulting deactivation or release of the interlock the mechanical coupler may remain stationary whereas at least one of the first part and a second part of the spray delivery device will be displaced under the action of the relaxing biasing member. If the mechanical biasing member is operably engaged with the mechanical coupler and the moveable part of the spray delivery device, the container of the spray delivery device is typically fixed inside the housing. When the biasing member is operably engaged with the mechanical coupler and the container of the spray delivery device it is typically the moveable part of the spray delivery device that is fixed inside the housing of the fluid dispensing device.

According to another example the spray delivery device or a portion thereof is arranged inside or attached to the housing of the fluid dispensing device. Typically, the spray delivery device comprises a first part, e.g., a movable part and a second part, e.g., a container. One of the first part and the second part, e.g., one of the container and the moveable part is then engaged with or is attached to one of the mechanical coupler and the biasing member. The other one of the mechanical coupler and the biasing member not being engaged or being attached to one of the mechanical coupler and the biasing member is typically fixed inside the housing.

With some examples the second part of the device, e.g., the container is stationary fixed inside the housing. Here, the second part, e.g., the moveable part is operably engaged with at least one of the biasing member and the mechanical coupler. With another example it is the first part, e.g., the moveable part that is fixed inside the housing of the fluid dispensing device. Then, at least one of the biasing member and the mechanical coupler is engaged with, attached to or fixed to the second part of the spray delivery device, e.g., fixed to the container. With any configuration the biasing member is operable to provide a dispensing force which is effective to induce a displacement or movement of the first part relative to the second part of the spray delivery device.

According to an example, the spray delivery device comprises a movable part and a container, wherein the container provides a reservoir for the fluid. The movable part is displaceable relative to the container between a preload position and a discharge position. The spray delivery device further comprises the outlet as described above. Moving of the movable part relative to the container is effective to discharge the spray jet from the outlet. With some examples the outlet is integrally formed with the movable part. The outlet will then be movable relative to the container. With other example, the outlet is stationary relative to the container. Then, the movable part is movable relative to the both, the outlet and the container.

Typically, the container of the spray delivery device is at least partially filled with a drug or medicament. The container may comprise a prefilled container being prefilled with the respective drug or medicament. The container and hence the entire spray delivery device may be preassembled inside the housing and hence inside the fluid dispensing device.

According to a further example at least one of the outlet and the container of the spray delivery device is fixed inside the housing of the fluid dispensing device. Here, the moveable part of the spray delivery device is mechanically engaged with or is connected to one of the mechanical coupler and the biasing member. In this way, a biasing member-induced displacement of the moveable part relative to the container of the spray delivery device can be provided.

With another example the outlet of the spray delivery device is fixed to the moveable part of the spray delivery device. Then, the container of the spray delivery device is mechanically engaged with or is connected to one of the mechanical coupler and the biasing member. While the outlet and the moveable part of the spray delivery device are both fixed relative to each other as well as to the housing of the fluid dispensing device it is the container of the spray delivery device that is mechanically engaged, hence fixed or connected to one of the mechanical coupler and the biasing member. In this way the biasing member may either directly or indirectly, i.e., via the mechanical coupler, induce a displacement, e.g., a longitudinal motion of the container relative to the moveable part of the spray delivery device. In this way, a dose of the fluid can be dispensed.

The outlet and the moveable part may be mutually connected or they may be integrally formed. Hence, the outlet may be incorporated or integrated into the moveable part. It is then of particular benefit, that the outlet and/or the moveable part of the spray delivery device is connected to the housing of the fluid dispensing device, typically the outlet of the spray delivery device directly communicates with the nozzle of the fluid dispensing device in a fluid transferring way.

In another aspect the present disclosure relates to a fluid dispensing device. The fluid dispensing device comprises a housing. The housing comprises an orifice and the housing is configured to accommodate at least a portion of a spray delivery device. The spray delivery device comprises an outlet through which the fluid stored in the spray delivery device can be discharged. The fluid dispensing device further comprises a protective cap detachably and/or movably arranged on the housing. The protective cap is at least one of transferable or displaceable into an opening position relative to the housing. In the opening position the protective cap uncovers or reveals the orifice. The protective cap is at least one of transferable or displaceable into a closing position relative to the housing. In the closing position the protective cap, i.e., at least a cap portion thereof covers the orifice of the housing.

The fluid dispensing device further comprises a mechanical biasing member reversibly transferable between a preloaded state and an unloaded state. The mechanical biasing member is configured to store mechanical energy in the pre-loaded state effective to produce a spray discharge of the spray delivery device. The fluid dispensing device further comprises a releasable interlock configured to retain the biasing member in the pre-loaded state. The device further comprises a manually actuatable trigger operationally engaged with the interlock and configured to release the interlock when actuated.

The protective cap or at least a portion thereof is configured or operable to actuate the trigger.

With some examples, the protective cap is operable to actuate the trigger as the protective cap approaches or reaches the opening position. This applies where the protective cap is movably or displaceably connected to the housing. With some examples, the protective cap is pivotally attached to the housing. Transferring of the protective cap from the closing position into the opening position includes pivoting of the protective cap from the closing position into the opening position.

With some examples the manually actuatable trigger is located in a recessed portion of the housing or in a recess of the housing. In this way the manually actuatable trigger cannot be depressed by a user. Instead, a specific tool is required to enter the recess of the housing in order to reach and/or to activate the manually actuatable trigger. The protective cap may be provided with a respective tool. In particular, the protective cap may comprise a protrusion sized to fit into the recess of the housing in order to mechanically engage with the manually actuatable trigger. The protrusion may form or constitute the tool. The protective cap may comprise a protrusion extending outwardly from an outside surface of the protective cap. Before or when reaching the opening position, the protrusion is configured to enter the recess of the housing and to engage the manually actuatable trigger.

When the protective cap is pivotally attached to the housing by a hinge with a hinge axis, a radial distance of the protrusion to the hinge axis is somewhat equal or equivalent to a radial distance of the recess to the hinge axis.

Generally, arranging the manually actuatable trigger in a recess or recessed portion of the housing and depression of the trigger by a protrusion of the protective cap may be implemented both by a protective cap being detachably connectable to the housing and by a protective cap being pivotally connected to the housing.

With some examples, since the manually actuatable trigger is located in a recessed portion of the housing it is effectively prevented from becoming actuated as long as the protective cap covers the orifice or as long as the protective cap is not in the opening position.

With some examples the interlock comprises a slider. The slider being slidably engaged with the housing. It may be guided by a guiding structure of the housing between an interlock position and a release position. In the interlock position the interlock is mechanically engaged with the at least one of the spray delivery device and a mechanical coupler configured to receive the spray delivery device. In the release position or release configuration the slider allows and supports a movement of the spray delivery device or at least a portion thereof, which movement is effective to produce the spray discharge of the spray delivery device. The mechanical coupler may be further engaged with the pre-loaded mechanical biasing member.

The slider may be displaceable from the interlock position into the release position along a first direction of movement. The mechanical coupler and/or the spray delivery device may be displaceable from a pre-loaded or cocked state into an unloaded or released state along a second direction of movement. The first direction of movement and the second direction of movement extend at a nonzero angle with respect to each other. The first direction of movement may extend at an angle of about 90° from the second direction of movement.

Movement of the mechanical coupler from the pre-loaded or cocked state towards and/or into the unloaded or release state is effectuated by the mechanical biasing member, e.g., by a spring.

The mechanical biasing member may comprise a first end in abutment or engagement with the mechanical coupler. The mechanical biasing member comprises a second end, opposite the first end in abutment or engagement with the housing of the fluid dispensing device.

For engagement with the mechanical biasing member the mechanical coupler may comprise an abutment section or a flange facing towards the second direction of movement. With some examples, the mechanical coupler comprises a tubular or cylindrical sleeve comprising a radially outwardly protruding flange section or comprising radially outwardly protruding struts. The mechanical biasing member may then extend along the longitudinal axis of the sleeve of the mechanical coupler. It may surround the mechanical coupler and may abut in axial or longitudinal direction with the radially outwardly protruding flange section or struts.

With some examples, the mechanical coupler and/or the spray delivery device comprises an abutment for engagement with the interlock. For this, the interlock may comprise a counter abutment complementary shaped to the abutment of the mechanical coupler or of the spray delivery device. The abutment of the mechanical coupler and/or of the spray delivery device and the counter abutment of the interlock are configured to block a movement of the mechanical coupler and/or of the spray delivery device relative to the interlock along the second direction of movement. In this way, the mechanical coupler and/or the spray delivery device can be effectively kept and/or secured in the pre-loaded state or position.

Movement or deformation of the manually actuatable trigger along the second direction of movement brings the abutment and the counter abutment out of engagement, thereby releasing the mechanical coupler and/or the spray delivery device. The mechanical coupler or the spray delivery device may then become subject to a movement along the first direction of movement under the effect of the mechanical biasing member.

With some examples, the mechanical coupler comprises more than one abutment. There may be provided numerous abutments, e.g., equidistantly arranged along the outside surface of the mechanical coupler. At least two abutments may be provided at diametrically opposite positions of the mechanical coupler. The at least two abutments may protrude outwardly from a sleeve or barrel of the mechanical coupler. Both abutments may simultaneously engage with the counter abutment provided by the body of the interlock, e.g., by the aperture thereof. By having two or more apartments a rather precise and tilt-free interlock can be provided for the mechanical coupler.

With some examples the slider of the interlock member is displaceable from the interlock position into the release position against the action of a return spring. In this way and when moved from the interlock position into and/or towards the release position the return spring is biased and stores mechanical energy. As soon as an external force is no longer present, which force causes the movement of the manually actuatable trigger towards the release position, the return spring serves to return the manually actuatable trigger back into the interlock position.

With some examples the interlock comprises an aperture sized to receive at least one of the mechanical coupler and the spray delivery device there through. In the interlock position the interlock is misaligned with regards to the position or dimension of the mechanical coupler and/or of the spray delivery device. Then, an edge of the aperture, e.g., constituting the counter abutment, is engaged with the abutment of the mechanical coupler.

A trigger-induced movement or deformation of the interlock serves to align the aperture of the interlock with the mechanical coupler so that the abutment between the mechanical engagement between the abutment and the counter abutment is abrogated and the mechanical coupler and/or other spray delivery device are allowed to enter order to intersect the aperture of the interlock.

With some examples the aperture of the interlock comprises a mechanical code or a keyed structure correspondingly shaped to a counter mechanical code or counter keyed structure on the outside surface of the mechanical coupler and/or of the spray delivery device. As long as the interlock is in the interlock position or interlock configuration the mechanical code or keyed structure of the interlock is misaligned or is offset from the counter mechanical code or counter keyed structure. In this way, the side edge of the aperture of the interlock blocks a movement of the mechanical coupler and/or of the spray delivery device along the second direction of movement.

A movement or deformation of the interlock relative to the mechanical coupler and/or relative to the spray delivery device brings the mechanical code or keyed structure of the interlock in alignment with the counter mechanical code or counter keyed structure of the mechanical coupler. Then, a movement of the mechanical coupler along the second direction of movement is no longer blocked by the interlock. The mechanical coupler and/or the spray delivery device or portions thereof can then be moved under the action of the relaxing or on biasing mechanical biasing member.

With some examples the interlock comprises a resiliently deformable ring structure comprising an aperture sized to receive at least one of the mechanical coupler and the spray delivery device. The resiliently deformable ring structure may comprise an oval shape. When and as long as the interlock is in the interlock position or interlocked configuration the ring structure is of a first ellipticity. When resiliently deformed towards and/or into the release position or release configuration the ring structure is of a second ellipticity. The second ellipticity is less than the first ellipticity. In other words, the second ellipticity resembles more a circular structure than the first ellipticity. The differences in length between long and short axes of the ring structure in the first ellipticity is larger than with the ring structure in the second ellipticity.

With a resiliently deformable ring structure the interlock may tend to assume an initial oval shape in the absence of deformation forces that could be applied through the manually actuatable trigger. The interlock may then have the tendency to automatically return into the interlock position or interlocked configuration. Here, a separate return spring becomes superfluous.

Typically, an outer end of the oval-shaped deformable ring structure which is located at a longitudinal end of a long axis of the oval is in mechanical engagement or is integrally formed with the trigger. An oppositely located end of the ring structure may be supported or may be in abutment with the housing of the fluid dispensing device. Then, by depressing the trigger inwardly, the distance between opposite ends separated from each other along the long axis of the oval of the ring structure is reduced and the distance between opposite ends of a short axis of the oval is increased. This increase of the short axis of the oval is induced by the depression of the manually actuatable trigger. Furthermore, the increase in length of the short axis is to such an extent, that the inner diameter or inner cross-section along the short axes is equal to or larger than the respective outside dimensions of the mechanical coupler and/or of the spray delivery device.

With some examples, the manually actuatable trigger is a portion of the releasable interlock and/or of the oval-shaped deformable ring structure of the interlock. In this way, the number of parts required for assembling the fluid dispensing device can be reduced to a minimum.

It is to be noted, that any features and effects disclosed herein in connection with an aspect or an example equally apply to all other aspects and examples as disclosed herein unless such features or effects mutually exclude.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, various benefits, effects and features of numerous examples of the fluid dispensing device are described in more detail by making reference to the drawings, in which:

FIG. 38 is illustrative of a first type of a spray delivery device in an initial configuration, FIG. 39 shows the spray delivery device of FIG. 38 during a dispensing operation and FIG. 40 is illustrative of the device of FIGS. 38 and 39 during a recovery, FIG. 41 shows a second type of a spray delivery device in an initial configuration, FIG. 42 shows the spray delivery device of FIG. 41 during a dispensing operation, FIG. 43 shows the spray delivery device of the second type during a recovery.

DETAILED DESCRIPTION

Figure 1:
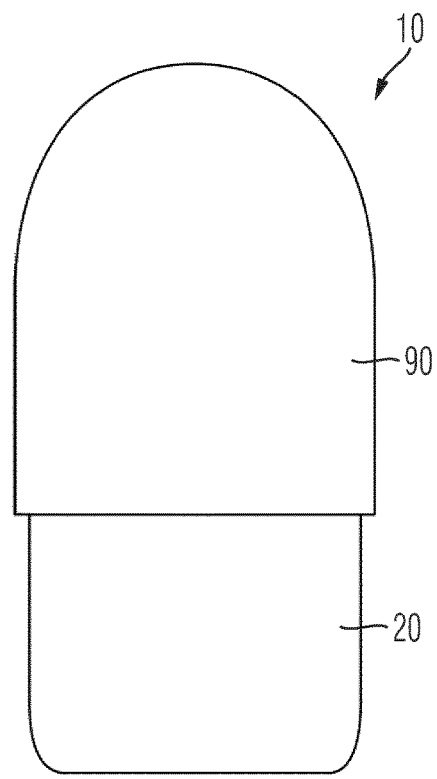
FIG. 1 is a schematic side view of one example of a fluid dispensing device.
Figure 2:
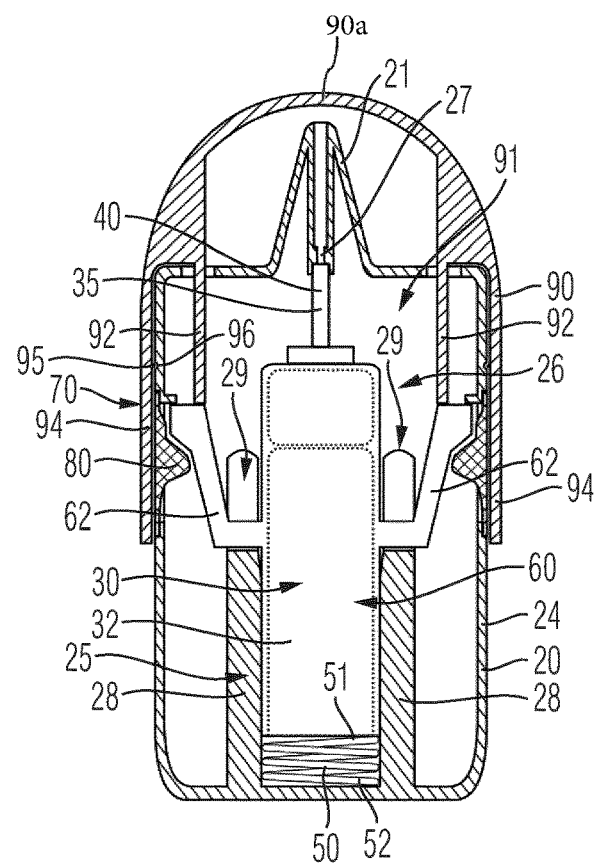
FIG. 2 is a cross-section through the device according to FIG. 1.

FIG. 1 illustrates a side view of one example of a fluid dispensing device 10 configured as a nasal inhaler. The fluid dispensing device 10 comprises a housing 20. The housing 20 is configured to accommodate a spray delivery device 30 as illustrated in the cross-section of FIG. 2. The housing 20 comprises an orifice 21 at an upper end or distal end configured to dispense an amount of a fluid provided in or provided by the spray delivery device 30. The fluid dispensing device 10 further comprises a protective cap 90. In the closing position as illustrated in FIG. 2 the protective cap 90 covers the entire upper section or upper end of the housing 20 and particularly covers the orifice 21.

It is generally sufficient, that only a portion of the protective cap 90, i.e., a cap portion 90a covers at least a part of the orifice 21. In the closing position as illustrated in FIGS. 1 and 2 an interior space 91 of the cup-shaped protective cap 90, e.g., comprising a hollow interior effectively covers the orifice 21.

Inside the housing 20 there is provided an accommodation space 26 configured to receive and to hold at least a part of the spray delivery device 30. The spray delivery device 30 may be preassembled inside the housing 20 or may be replaceably assembled and arranged inside the housing 20. The spray delivery device 30 as illustrated in FIG. 2 is representative of either a first or second type of spray delivery device as will be explained in greater detail with respect to FIGS. 38-43.

In FIGS. 38-40 a first type of a spray delivery device 30 is illustrated. In FIGS. 41-43 a second type of a spray delivery device 130 is illustrated. The spray delivery device 30 comprises a container 32 configured to receive and to hold an amount of a liquid substance, e.g., a fluid intended for dispensing. The spray delivery device 30 further comprises a moveable part 35 that is moveable relative to the container 32. The spray delivery device 30 further comprises an outlet 40. With the first type of spray delivery device 30 as illustrated in FIGS. 38-40 the moveable part 35 and the outlet 40 are mutually connected and fixed. They may even be integrally formed. Here, the outlet 40 can be regarded as a first part of the spray delivery device 30 and the container 32 can be regarded as a second part of the spray delivery device 30.

Optionally, the spray delivery device 30 further comprises a base 45 that is attached to an upper or outlet end of the container 32. The container 32 is open towards the base 45. The base 45 further comprises a hollow chamber 38. A tube 31 is connected to the base 45. The tube 31 may be implemented as a suction tube and extends into the interior of the container 32. The tube 31 is in flow connection with the hollow chamber 38. Inside or outside the chamber 38 there is provided a spring 42. The spring 42 is configured to bias the moveable part 35 away from the container 32, hence in an upright or upwards direction as illustrated in FIG. 38. The base 45 is further equipped with an inlet valve 33. The inlet valve 33 is arranged between the tube 31 and the chamber 38. The base 45 further comprises an outlet valve 36 that is arranged between the chamber 38 and the outlet 40. As illustrated in FIG. 38, the upper or free end of the moveable part 35 is in flow communication with the chamber 38 through an elongated and rigid hollow shaft 41.

In an initial configuration as illustrated in FIG. 38 the chamber 38 is filled with the liquid substance withdrawn from the interior of the container 32. If a user now applies a pressure onto the moveable part 35 effective to move the moveable part 35 towards the container 32 the shaft 41 enters the chamber 38 displaces the fluid located inside the chamber 38. The fluid can only escape via the hollow shaft 41 towards the outlet 40. During the displacement of the moveable part 35 relative to the container 32 the inlet valve 33 is closed thus impeding that the fluid located inside the chamber 38 could re-enter the container 32.

After release of the moveable part 35 the spring 42 is operable to drive the moveable part 35 and the container 32 apart from each other. In the configuration as illustrated in FIG. 40, the spring 42 is operable to displace the moveable part 35 away from the container 32. This leads to an under pressure in the chamber 38 and thus to a suction-based withdrawal of a further dose of the fluid from the container 32 through the tube 31 and into the chamber 38. Then, the chamber 38 is filled again and the spray delivery device 30 of the first type is ready for a subsequent dispensing procedure that may be initiated by repeatedly depressing or displacing the moveable part 35 relative to the container 32.

The spray delivery device 130 of the second type as illustrated in FIGS. 41-43 works in accordance to a similar principle. Similar or like components compared to the spray delivery device 30 as illustrated in FIGS. 38-40 are provided with the same reference numbers increased by 100. Also here, the spray delivery device 130 comprises a container 132, a moveable part 135 and an outlet 140. The spray delivery device 130 further comprises a base 145 attached to an outlet end of the container 132. A tube 131 connected to a chamber 138 of the spray delivery device 130 is arranged inside the interior of the container 132. Between the chamber 138 and the tube 132 there is provided an inlet valve 133.

An outlet valve 136 is provided at the free end of the outlet 140. The outlet valve 136 may be implemented as a duckbill valve.

The working principle of the second type of the spray delivery device 130 is comparable to the working principle of the first type of spray delivery device 30. In an initial configuration as illustrated in FIG. 41 the chamber 138 is filled with the fluid. But here and contrary to the first type of spray delivery device 30 the outlet 140 is fixed to the base 145. Rather, the moveable part 135 is displaceable relative to the container 132 as well as relative to the outlet 140 against the action of the spring 142. As indicated in FIGS. 41-43, the base 145 provides an elongated hollow shaft in which the moveable part 135 is allowed to slide under and against the action of the spring 142.

As the moveable part 135 is depressed the moveable part 135 at least partially enters the chamber 138 and displaces the liquid contained therein. During this motion as illustrated in FIG. 42 the inlet valve 133 is closed. So, the liquid can only be expelled through the hollow and rigid shaft 141 towards the outlet 140. The outlet valve 136 allows and supports dispensing and/or atomization of the fluid.

Thereafter and upon release of the moveable part 135 the relaxing spring 142 is effective to displace the moveable part 135 away from the container 132. Since the outlet valve 136 is effectively closed the spring-induced movement of the moveable part 135 leads to the build-up of a negative pressure inside the chamber 138. The negative pressure serves to open the inlet valve 133 and to withdraw a further amount of the liquid from the interior of the container 132 into the chamber 138. Here, the movable part 135 can be regarded as a first part of the spray delivery device 130 and at least one of the outlet 140 and the container 132 can be regarded as a second part of the spray delivery device.

It should be noted, that both of the first and second types of spray delivery devices 30, 130 are equally applicable to the numerous examples of fluid dispensing devices 10, 100 as described herein.

For a dispensing operation it is only required that the moveable part 35, 135 is subject to a displacement relative to the container 32, 132.

Returning to the example of the fluid dispensing device 10 as illustrated in FIGS. 1-5 the spray delivery device 30 of the first type is assembled inside the accommodating space 26 of the housing 20. Here, the outlet 40 of the spray delivery device 30 is connected or fixed to the orifice 21. At least one of the outlet 40 and the orifice 21 comprise a jet nozzle 27 having a reduced diameter effective to atomize a streamlet of the fluid dispensed through the outlet 40.

With all examples as illustrated herein, the orifice 21 of the housing 20 of the fluid dispensing device is in alignment with the outlet 40, 140 of the spray delivery device 30, 130.

Even though not illustrated there might be further examples, wherein the orifice 21 provides a through opening for the outlet 40, 140 of the spray delivery device 30, 130. Here, the outlet 40, 140 may extend and reach through the orifice 21. With other examples, the orifice 21 may comprise a comparatively large opening in the housing 20, having a cross section that is larger in size than a cross-section of the spray delivery device 30, 130. Here, the orifice 21 may provide and enable a removal of the spray delivery device 30, 130 from the housing 20. The orifice 21 may be sized and configured to enable insertion of the spray delivery device 30, 130 from outside the housing 20 into the housing 20.

With a further example, the orifice 21 of the fluid dispensing device 10, 100 may be provided by the outlet 40, 140 of the spray delivery device 30, 130. Thus, the orifice 21 of the fluid dispensing device 10, 100 may coincide with the outlet 40, 140 of the spray delivery device 30, 130; and vice versa.

In the example of FIGS. 1-5, the outlet 40 is connected to or is integrally formed with the moveable part 35 of the spray delivery device 30. The spray delivery device 30 is mechanically engaged with a mechanical coupler 60. The mechanical coupler 60 is a component of the fluid dispensing device 10. The mechanical coupler 60 is engaged with a biasing member 50. The biasing member is presently configured as a compression spring having a first end 51 in abutment or engagement with the mechanical coupler 60 and further having a second end 52 opposite to the first end 51 that is in engagement or in abutment with the housing 20.

Figure 3:
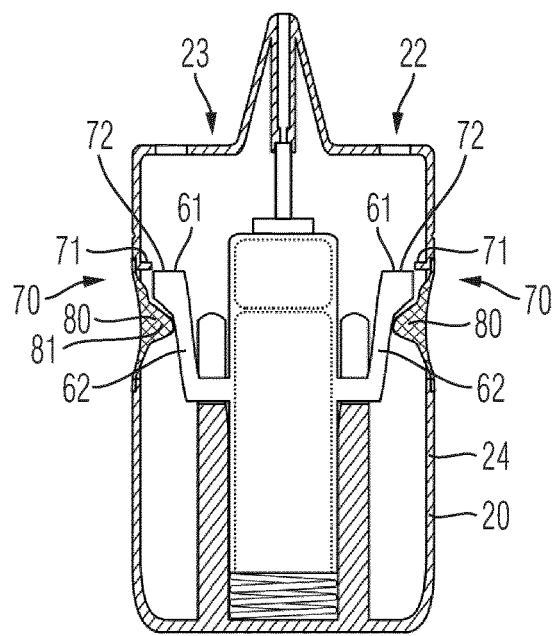
FIG. 3 shows the fluid dispensing device after removal of a protective cap and after actuation of a trigger.
Figure 4:
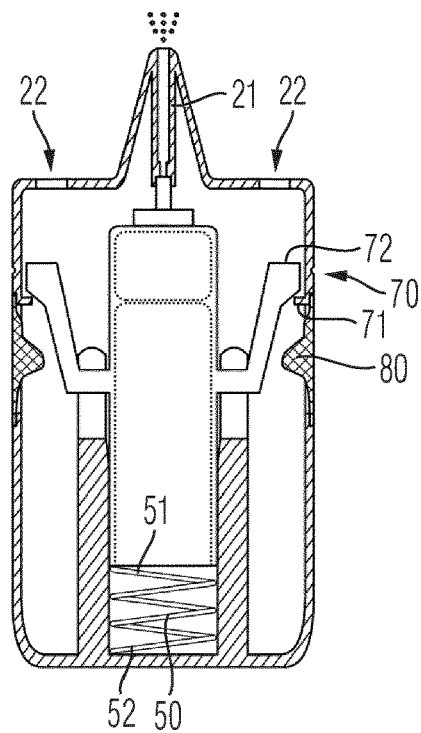
FIG. 4 shows the device of FIG. 3 during or after execution of a dispensing operation.
Figure 5:
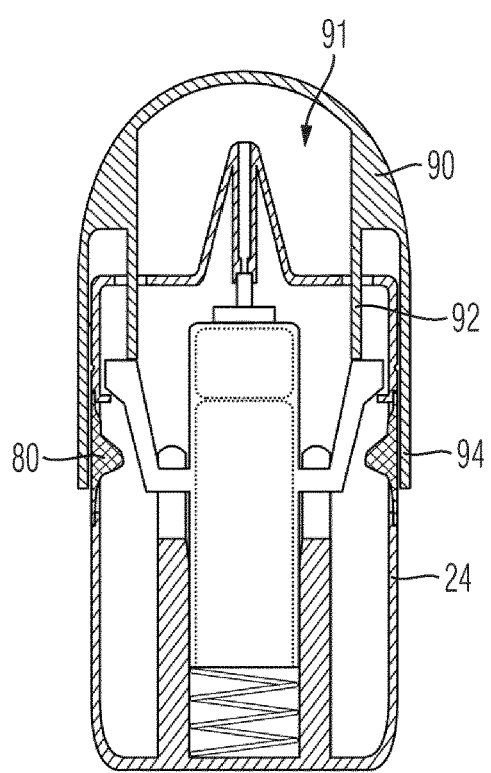
FIG. 5 shows the device of FIGS. 2-4 before or during reattachment of the protective cap.

Under the effect of the biasing member 50 the mechanical coupler 60 is displaceable from a preload position as illustrated in FIGS. 2 and 3 into an unload position as illustrated in FIGS. 4 and 5. The mechanical coupler 60 is displaceable from the unload position into the preload position against the action of the biasing member 50. In the presently illustrated example the biasing member 50 is located and arranged between a bottom of the housing 20 and a bottom of the mechanical coupler 60. The container 32 and optionally also the base 45 of the spray delivery device 30 are fastened to or fixed to the mechanical coupler 60. Insofar, a movement of the mechanical coupler 60 relative to the housing 20 leads to a movement of the container 32 relative to the outlet 40 and thus to the dispensing of a dose of the fluid from the spray delivery device 30.

The mechanical coupler 60 is slidably displaceable inside the housing 20 in accordance to a longitudinal guiding structure 25. As illustrated in FIG. 2 the guiding structure 25 comprises at least two or even more shaft portions 28 extending parallel to a surface normal of a bottom of the housing 20. The shaft portions 28 enclose the mechanical coupler 60. Therefore, a side guiding structure 25 defines a longitudinal direction along which the mechanical coupler 60 is slidably displaceable relative to the housing 20 under and against the action of the biasing member 50. Instead of at least two or more shaft portions 28 the housing 20 may comprise a hollow sleeve extending into the accommodation space 26 and being configured and sized to slidably receive the mechanical coupler 60 therein.

The fluid dispensing device 10 further comprises an interlock 70 that is operable to retain the mechanical coupler in the preload position as illustrated in FIGS. 2 and 3. The interlock 70 is further operable to retain the biasing member 50 in the pre-loaded state as illustrated in FIGS. 2 and 3. The fluid dispensing device 10 further comprises a trigger 80 that is operably engageable with the interlock 70 in order to release the interlock 70 and to enable unbiasing or unloading of at least one of the biasing member 50 and the mechanical coupler 60.

As shown in FIGS. 2-5 the mechanical coupler 60 comprises at least one strut 62 extending outwardly from the outer circumference of the, e.g., cylindrically-shaped mechanical coupler 60. The mechanical coupler 60 as illustrated in FIGS. 2-5 comprises at least two diametrically oppositely located struts 62 each of which extending through a slit or aperture provided in the guiding structure 25, hence in the shaft portions 28 of the guiding structure 25. The two slits 29 or grooves are provided near an upper free end of the shaft portions 28. They provide a well-defined longitudinal guiding of the mechanical coupler 60 relative to the housing 20. The struts 62 both comprise an abutment 61 facing towards a distal or upper end of the housing 20.

The interlock 70 comprises by a catch feature 71 provided on an inside of the housing 20 and a correspondingly or complementary-shaped snap feature 72 provided on the mechanical coupler 60. The snap feature 72 is provided on or at an end section of the strut 62 of the mechanical coupler 60. In an initial configuration and as illustrated in FIG. 2, the snap feature 72 of the mechanical coupler 60 is in direct abutment with the inwardly protruding catch feature 71 that is fixed to an inside of the housing 20. As it is apparent from a comparison of FIGS. 2 and 3, the struts 62 are elastically deformable such as to bring the catch feature 71 and the snap feature 72 out of mechanical engagement as illustrated in FIG. 3. Such a temporary deformation or pivoting of the snap feature 72 is obtained by depressing of the trigger 80.

The trigger 80 comprises an inwardly extending pin 81. The entire trigger 80 and/or its pin 81 may comprise a resilient material. Hence, the trigger 80 is depressible inwardly, hence into the interior of the accommodating space 26. The trigger 80 or both triggers 80 are operable to apply a respective inwardly directed force effect onto the interlock 70 and hence onto the inwardly deformable or inwardly pivotable struts 62 and are thus operable to bring the mutually corresponding snap features 72 and catch features 71 out of engagement. As long as the catch features 71 and the snap features 72 are in mutual abutment the respective engagement of the struts 62 with the housing 20 hinders and prevents a displacement of the mechanical coupler 60 towards the orifice 21.

As soon as the interlock 70 is released, e.g., by simultaneously depressing the oppositely located triggers 80, the respective interlocks 70 are released and the mechanical coupler 60 is allowed to become displaced towards the orifice 21 under the action of the relaxing biasing member 50 as illustrated in FIG. 4. As a consequence, a dose of the fluid is expelled through the orifice 21 due to the movement of the container 32 relative to the outlet 40.

Now and after a dose has been dispensed the protective cap 90 can be reassembled on the housing 20. The cup-shaped hollow cap 90 comprises a hollow interior 91 into which at least one longitudinal extension 92 extends. In the example as illustrated in FIGS. 2-5 the protective cap 90 comprises two longitudinally extending extensions 91 that may be configured as rods. The upper end or upper end face 23 of the housing 20 comprises at least one through opening 22. In the present example there are provided two through openings 22 each of which being longitudinally aligned with the position of the abutments 61 of the mechanical coupler 60.

As the protective cap 90 is reassembled onto the housing the longitudinal extensions 92 enter the through openings 22 and extend through the through openings 22 until the longitudinal extensions 92 get in mechanical engagement, hence in direct abutment with the abutments 61 of the struts 62 of the mechanical coupler 60. Such an abutment configuration as illustrated in FIG. 5 is obtained before the protective cap 90 reaches a closing position. Starting from this intermediate assembly configuration as illustrated in FIG. 5 the protective cap 90 is further displaceable or depressible downwardly, hence towards the bottom of the housing 20 thus urging the mechanical coupler 60 towards the bottom of the housing 20 and against the action of the biasing member 50 until the initial configuration as illustrated in FIG. 2 has been reached, in which the protective cap 90 is in the closing position. Upon or prior to reaching the closing position as illustrated in FIG. 2 the interlock 70 automatically locks. The snap features 72 re-engage with the catch features 71 and a spring-induced displacement of the mechanical coupler 60 is effectively prevented.

In this configuration the fluid dispensing device 10 can be stored until it is to be used for a proceeding dispensing action.

As it is apparent from a comparison of FIGS. 2 and 3 the trigger 80 is arranged flush in a sidewall 24 of the housing 20. An actuation of the triggers 80 as illustrated in FIG. 3 requires a depressing the triggers 80 further inwardly. The trigger or triggers 80 may be integrated into the sidewall 24. They do not protrude from the sidewall 24. This allows a rather smooth assembly of the protective cap 90 onto the housing to such an extent, that a sidewall 94 of the protective cap 90 effectively and/or entirely covers the triggers 80.

In the closing position as illustrated in FIG. 2, the two triggers 80 are neither accessible nor depressible from outside. They are effectively inoperable as long as the protective cap 90 is in the closing position. Operation or actuation of the triggers 80 and hence a release of the interlock 70 requires a detachment or an opening of the protective cap 90. It is only then and as illustrated in FIGS. 3 and 4, that the triggers 80 become accessible such that they can be depressed or actuated by a user of the device. In this way, the fluid dispensing device 10 can be stored in a pre-loaded or pre-cocked state without a substantial danger of an inadvertent, uncontrolled or premature release of a dispensing action.

The protective cap 90 is held in place in the closing position as illustrated in FIG. 2 by means of at least one fastener. Here, an interior of the sidewall 94 of the protective cap comprises at least one fastening feature 95 configured to engage and to cooperate with a correspondingly-shaped counter-fastening feature 96 provided on an outside surface of the housing 20. Typically, one of the fastening feature 95 and the counter-fastening feature 96 comprises a protrusion configured to engage with a correspondingly or complementary-shaped recess of the other one of the fastening feature 95 and the counter-fastening feature 96. The fastening feature 95 and the counter-fastening feature 96 are configured to form at least one of a positive connection and a frictional engagement. They may comprise mutually corresponding snap-or catch features.

Figure 6:
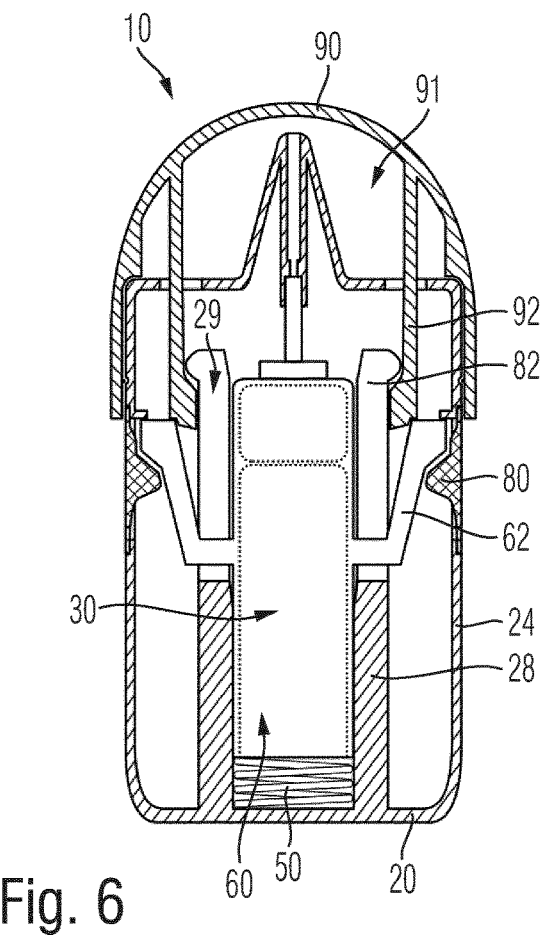
FIG. 6 shows a cross-section through a further example of a fluid dispensing device.
Figure 7:
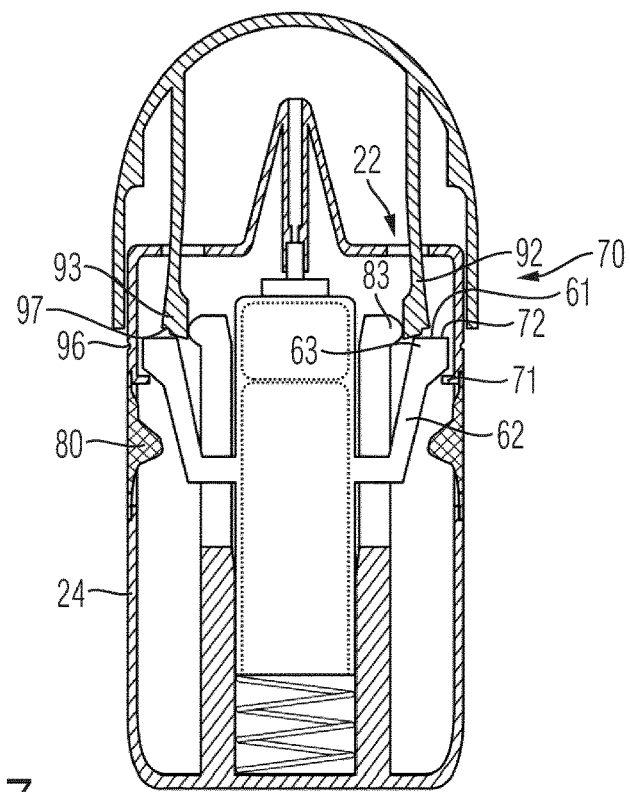
FIG. 7 shows the dispensing device of FIG. 6 during reattachment of the protective cap.

The further example as illustrated in FIGS. 6 and 7 slightly varies from the example as illustrated in FIGS. 2-5. Here, the longitudinal extension 92 of the protective cap 90 is shortened. In the closing position of the protective cap 90 as illustrated in FIG. 6 the longitudinal extensions 92 and hence the protective cap 90 is or are configured to impede a release of the interlock 70. Here, the triggers 80 are in fact accessible from outside the fluid dispensing device 10 when the protective cap 90 is mounted thereon and when the protective cap 90 is in the closing position.

The longitudinal extensions 92 of the protective cap are clamped between a support structure 82 and the struts 62. Here, the support structure 82 of the housing may be implemented as an extension of the shaft portion 28 as described above. The support structure 82 may provide a kind of a sidewall against which the longitudinal extensions 92 abut when the protective cap 90 has reached the closing position. In the closing position the longitudinal extensions 92 fill out a free space between the strut 62 and the support structure 82 of the housing 20. In this way, an inwardly directed movement of the struts 62 for disengaging or for releasing of the interlock 70 is effectively blocked and impeded.

In FIG. 7 an intermediate re-assembly configuration of the protective cap 90 is illustrated, wherein the free ends of the longitudinal extensions 92 become engaged with the abutments 61 of the struts 62. The longitudinal extensions 92 of the protective cap 90 comprise a thickened shoe section 93 at their free end. The upper end of the support structure 82 comprises an outwardly bulged portion 83. As the longitudinal extensions 92 with their shoe section 93 slide along the bulged portion 83 the shoe sections 93 experience a transverse, e.g., outwardly directed resilient deformation. At the same time and as the protective cap 90 is subject to a closing movement towards the bottom of the housing 20 the free end of the longitudinal extensions 92 applies a respective pressure on a corner section 63 of the struts 62. As the closing position has been reached, the shoe section 93 has passed the bulged portion 83 and is thus allowed to return transversely, e.g., to deflect inwardly, i.e., towards the center of the housing 20. Due to this elastic relaxation a recessed portion 97 at a corner section of the shoe section 93 at the free end of the longitudinal extensions 92 facing towards the sidewall 24 engages with a corner section 63 of the struts 62 thus locking the struts 62 in place.

Even though the triggers 80 are accessible from outside and even though the user can apply an inwardly directed pressure onto the triggers 80 they are ineffective to release the interlock 70 because the struts 62 are hindered to move inwardly to such an extent that mutually engaged snap features 72 and the catch features 71 would disengage.

Figure 8:
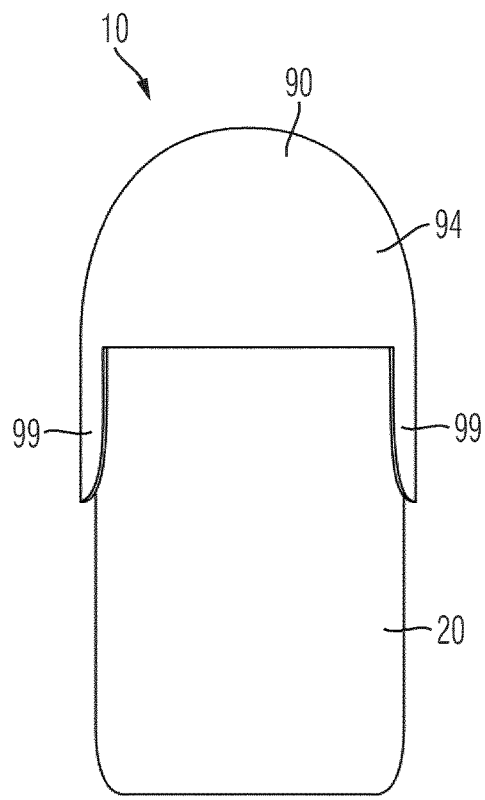
FIG. 8 shows a side view of a further example of a fluid dispensing device with a pivotable protective cap.
Figure 9:
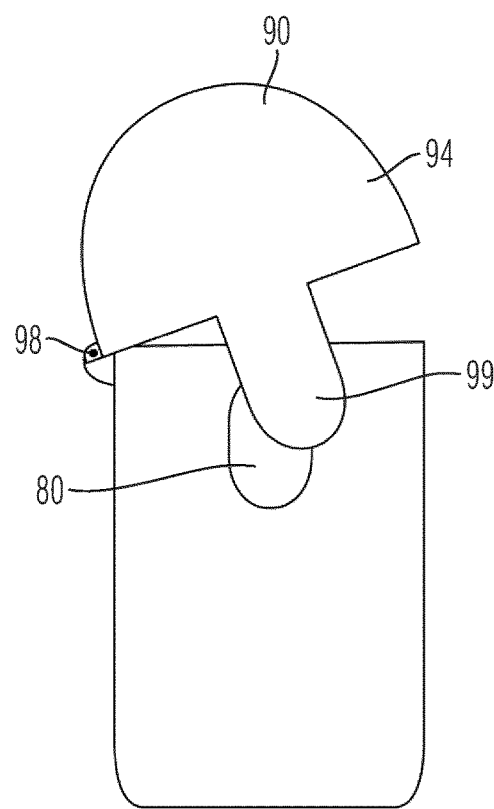
FIG. 9 shows another side view of the fluid dispensing device of FIG. 8 with the protective cap partially opened.

The illustrated examples of FIGS. 1-7 show an arrangement of the protective cap 90, wherein the cap 90 is entirely detachable from the housing 20. With the further examples as illustrated in FIGS. 8-19 the protective cap 90 is pivotally attached to the housing 20. It is pivotable with regard to a pivot axis 98 as illustrated in FIG. 9. For opening and closing the cap 90 it is hence to be pivoted with regard to the pivot axis 98. The protective cap 90 as illustrated in FIGS. 8 and 9 comprises a cup-shaped geometry with a hollow interior 91. Compared to the protective cap of FIGS. 1-8 the protective cap 90 as illustrated in FIGS. 8-13 comprises two longitudinal extensions 99 that are configured and operable to cover the trigger 80 when the protective cap 90 is in the closed configuration as, e.g., illustrated in FIG. 10. The extensions 99 protrude in longitudinal direction from a sidewall 94 of the protective cap. The working principle and the slidable support of the mechanical coupler 60 inside the housing 20 and the engagement between the cap 90 and the mechanical coupler 60 is substantially identical or equivalent to the examples as illustrated in FIGS. 1-7.

Figure 10:
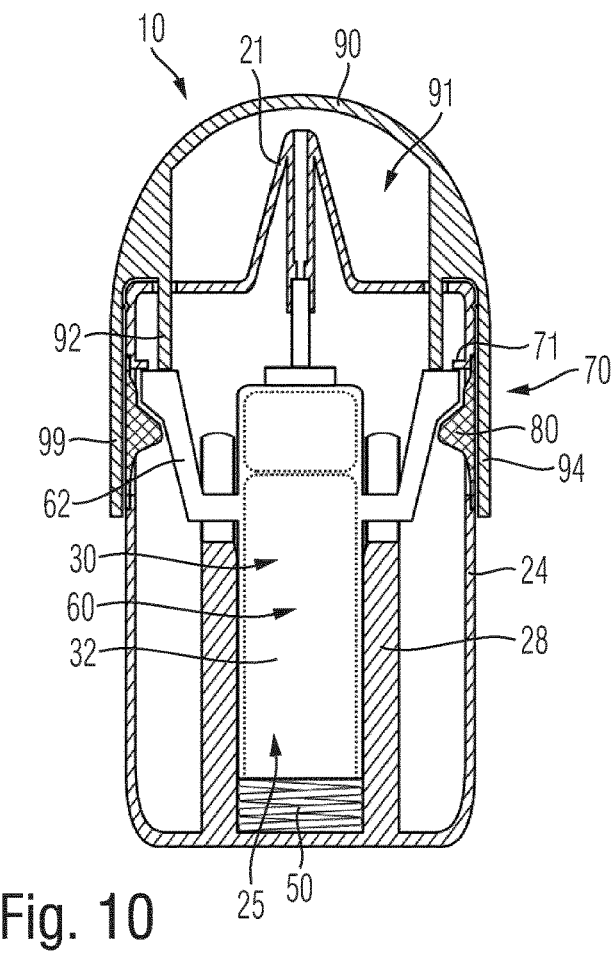
FIG. 10 shows the device of FIGS. 8 and 9 in cross-section with the protective cap in the closing position.
Figure 11:
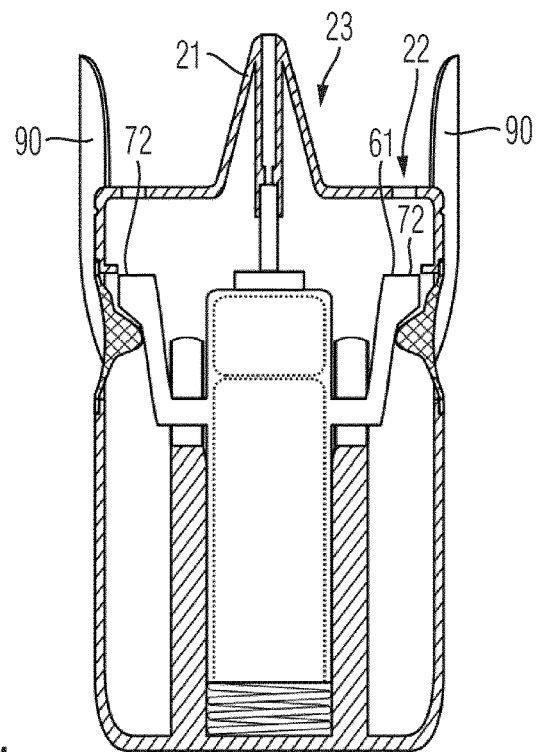
FIG. 11 shows the device of FIG. 10 with the protective cap in the opening position.
Figure 12:
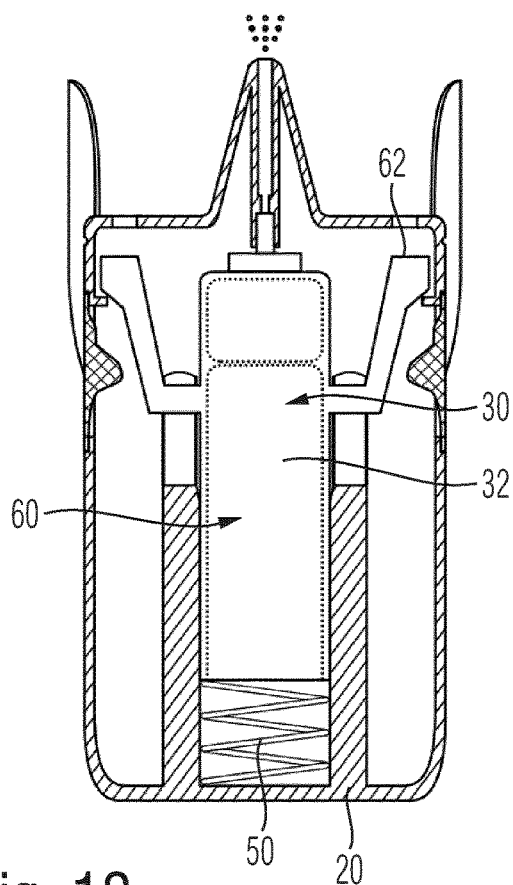
FIG. 12 shows the device of FIG. 11 after or during a dispensing operation and FIG. 13 shows the device of FIG. 12 during a closing operation of the protective cap.
Figure 13:
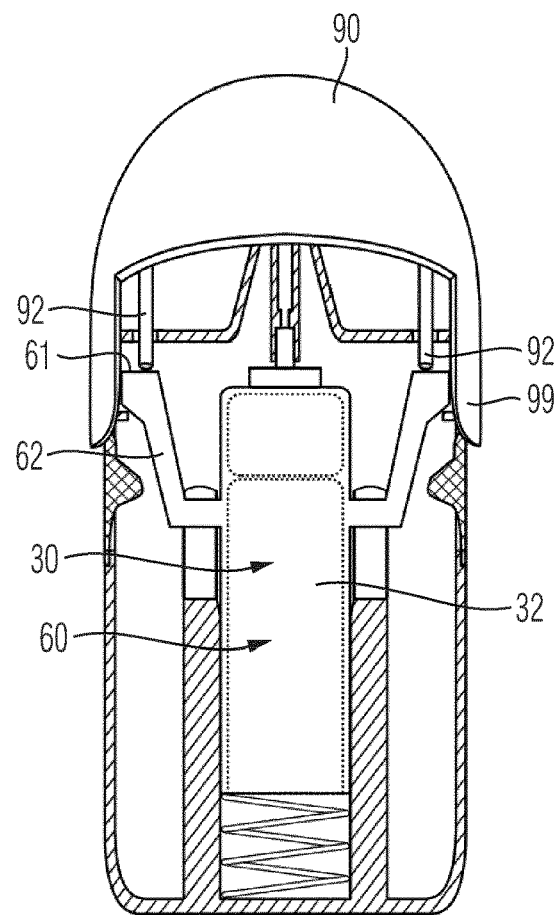
Figure 14:
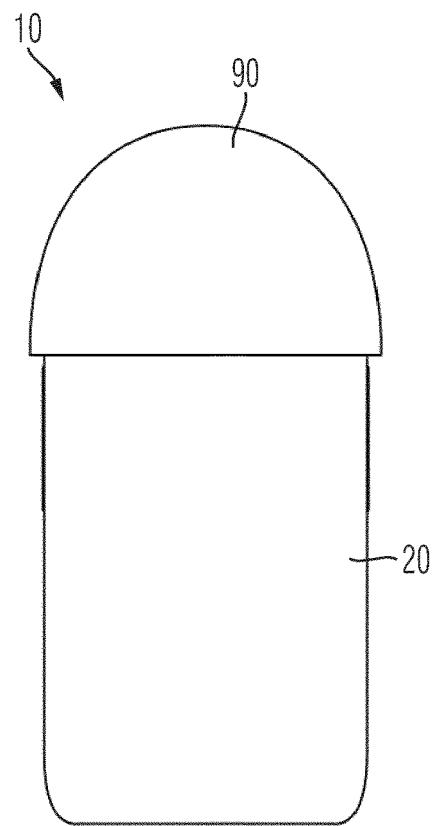
FIG. 14 shows a side view of another example of the fluid dispensing device comprising a pivotable cap.
Figure 15:
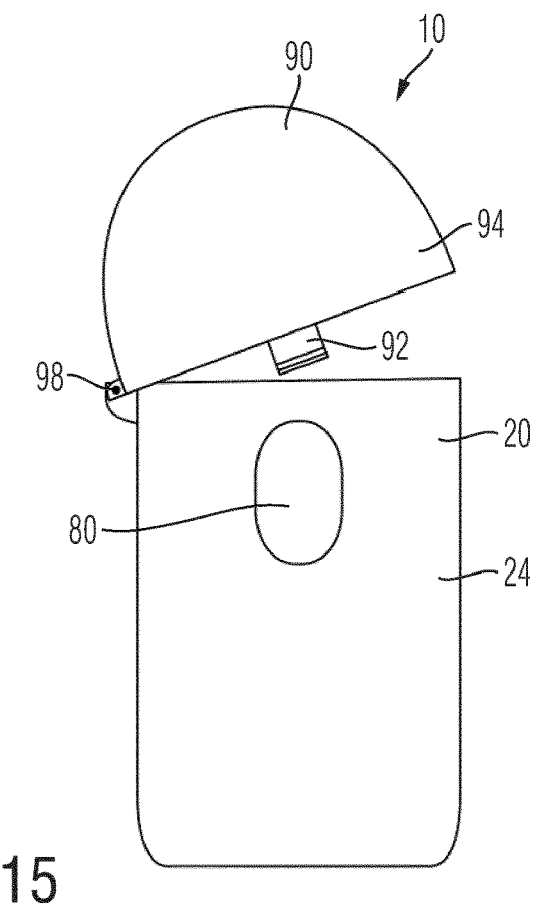
FIG. 15 shows the device of FIG. 14 in another side view with the protective cap partially opened.

Insofar, only the features of the example of FIGS. 8-13 that differ from the examples of FIGS. 2-5 are described in the following. In FIG. 10 an initial configuration is shown, wherein the sidewall 94 of the protective cap entirely covers the triggers 80 when in the closing position. Opening of the protective cap, hence pivoting the protective cap 90 with regard to the pivot axis 99 reveals and provides access to the triggers 80 that are integrated into or that are arranged flush in the sidewall 24 of the housing 20. In the closing position as illustrated in FIG. 10, the extensions 99 of the protective cap 90 cover the triggers 80.

Release of the interlock 70 by depression of the triggers 80 is implemented in the same way as described before with respect to FIG. 2-5. Compared to the examples of FIGS. 2-7 the through opening 22 provided in the upper end face 23 of the housing 20 is implemented as a longitudinal slit that extends perpendicular to the elongation of the pivot axis 98. In this way, the longitudinal extensions 92 of the protective cap 90 are allowed to enter the housing 20 through the elongated slits in accordance to the pivoting or swiveling motion of the protective cap 90.

In order to provide a sufficient mutual abutment between the free end of the longitudinal extensions 92 and the abutment 61 of the mechanical coupler 60 the abutment 61 and hence the struts 62 comprise an extension in a direction perpendicular to the pivot axis 98 that tolerates a motion of the free end of the longitudinal extensions 92 in radial direction, i.e., perpendicular to the pivot axis 98. This is to ensure, that when the longitudinal extensions 92 mechanically engage with the abutments 61 of the mechanical coupler 60 the engagement is maintained until the protective cap 90 reaches the closing position as illustrated in FIG. 10.

The further example as illustrated in FIGS. 14-19 is somewhat equivalent to the example as shown previously in FIGS. 6 and 7 with the exception, that the protective cap 90 is pivotally connected to the housing 20. Also here, the protective cap 90 is pivotable relative to the housing 20 with regards to a pivot axis 98. The sidewall 94 of the protective cap 90 is void of the extensions 99 as illustrated in FIG. 9. Instead, and similar as described with respect to FIGS. 6 and 7 the longitudinal extensions 92 of the protective cap 90 are configured to block a release of the interlock 70. Also here and because of a pivoting motion of the protective cap 90 between the opening position and the closing position the through openings 22 in the end face 23 of the housing 20 comprise an elongated slit so as to enable a pivoting insertion of the longitudinal extensions 92 of the cup-shaped protective cap 90.

Figure 16:
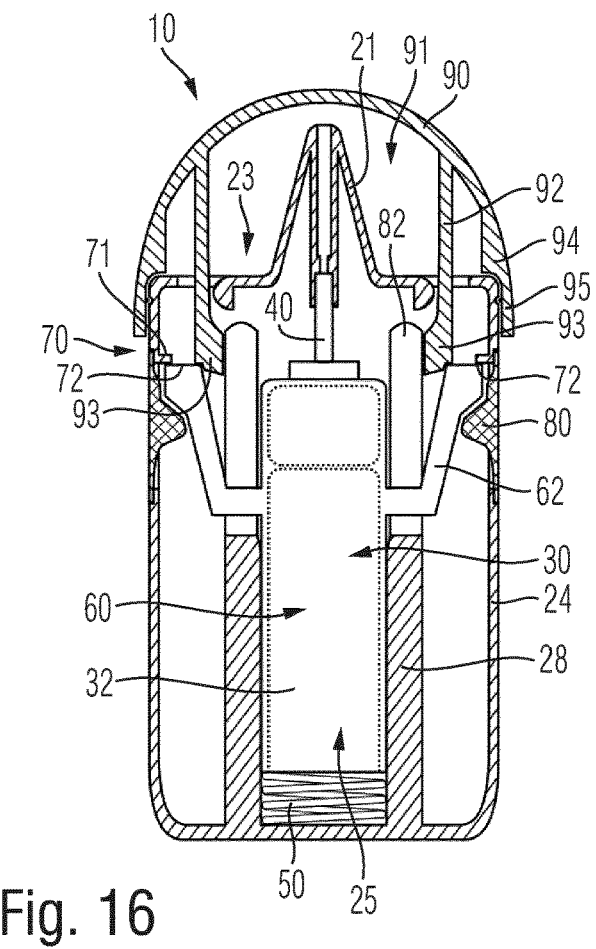
FIG. 16 shows a cross-section through the dispensing device of FIG. 14.

Also here, the triggers 80 are permanently accessible from outside and irrespective of a configuration or momentary position of the protective cap 90. As the protective cap 90 is assembled to the housing 20 and as it reaches a closing position as illustrated in FIG. 16 the shoe sections 93 of the long extensions 92 are located between the support structure 82 of the housing 20 and a portion of the strut section 62 facing towards the support structure 82. In this way, a laterally directed, e.g., an inwardly directed displacement of the struts 62 towards the support structures 82 is effectively blocked and impeded as long as the protective cap 90 is in the closing position.

Figure 17:
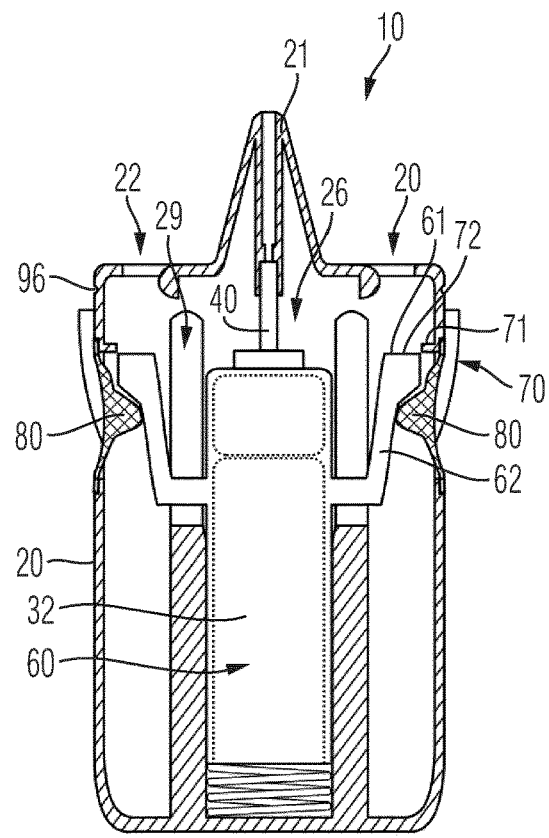
FIG. 17 shows the dispensing device of FIG. 16 with the protective cap in the opening position.
Figure 18:
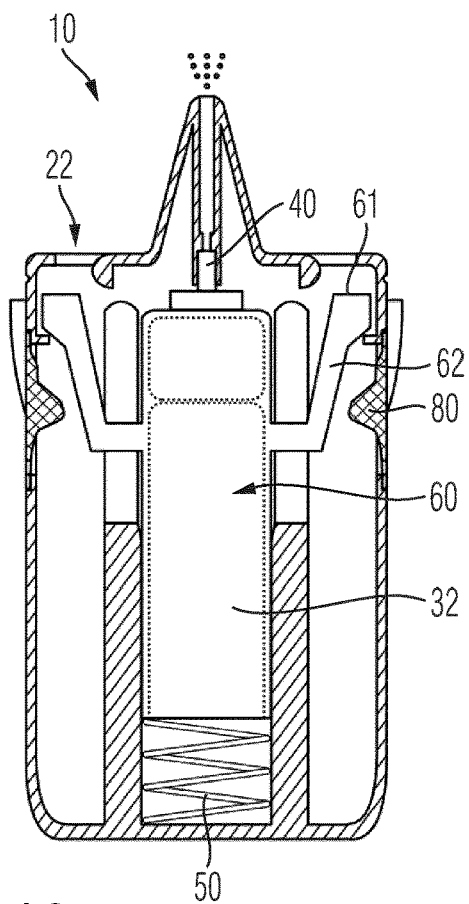
FIG. 18 shows the device of FIG. 17 after or during a dispensing operation and FIG. 19 is illustrative of the device of FIG. 18 during a closing operation of the protective cap.

It is only upon opening of the protective cap 90, i.e., by pivoting the protective cap 90 into the opening position that the longitudinal extensions 92 leave the accommodating space 26 and allow and trigger-induced displacement of the struts 62 by way of which the interlock 70 is released because the catch features 71 and the snap features 72 of the housing 20 and of the mechanical coupler 60 disengage as illustrated in FIG. 17. As a consequence and as shown in FIG. 18 the biasing member 50 is allowed to unbias and to displace the mechanical coupler 60 towards the orifice 21, thus inducing a movement of the container 32 relative to the outlet 40 by way of which a dose of the fluid is dispensed through the orifice 21 as illustrated in FIG. 18.

Figure 19:
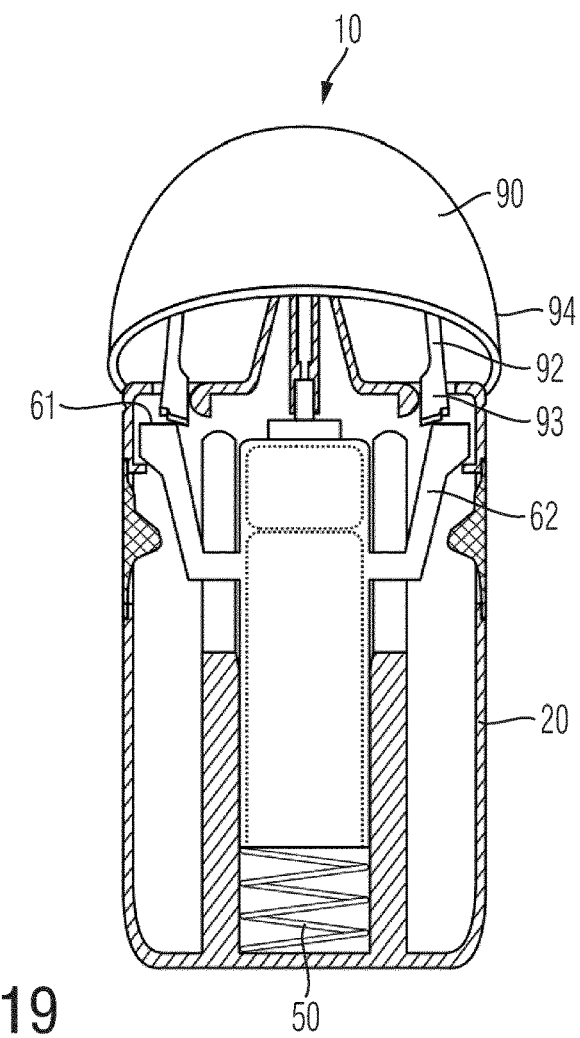

As the protective cap 90 is remounted onto the housing 20 and as the protective cap 90 is pivoted towards the closing position the longitudinal extensions 92 get in engagement with the abutment 61 of the struts 62 as illustrated in FIG. 19. Starting from this intermediate configuration as shown in FIG. 19, in which the longitudinal extensions 92 have just entered and reached through the through openings 22 a further closing pivoting motion of the protective cap 90 relative to the housing 20 leads to a longitudinal displacement of the struts 62 and hence of the mechanical coupler 60 against the action of the biasing member 50 until the closing position has been reached. Before or with reaching the closing position the interlock 70 is activated such that a repeated opening of the protective cap 90 has no effect on the dispensing of the fluid until the triggers 80 are depressed again.

In FIGS. 20-37 further examples of fluid dispensing devices 100 are illustrated that make use of a spray delivery device 130 of the second type. Here, the container 132 is fixed inside a housing 120 of the fluid dispensing device 100 whereas the moveable part 138 of the spray delivery device 130 is subject to a displacement or movement relative to the housing 120. As it will become apparent, the outlet 140 of the spray delivery device 130 is immobile relative to the container 132. It may be fixed to the container 132. Rather, the moveable part 135 is displaceable relative to both, the container 132 and the outlet 140. Also here, the outlet 140 is fixed to the housing 120. It is in fluid engagement with an orifice 121 provided at an upper end of the housing.

Figure 20:
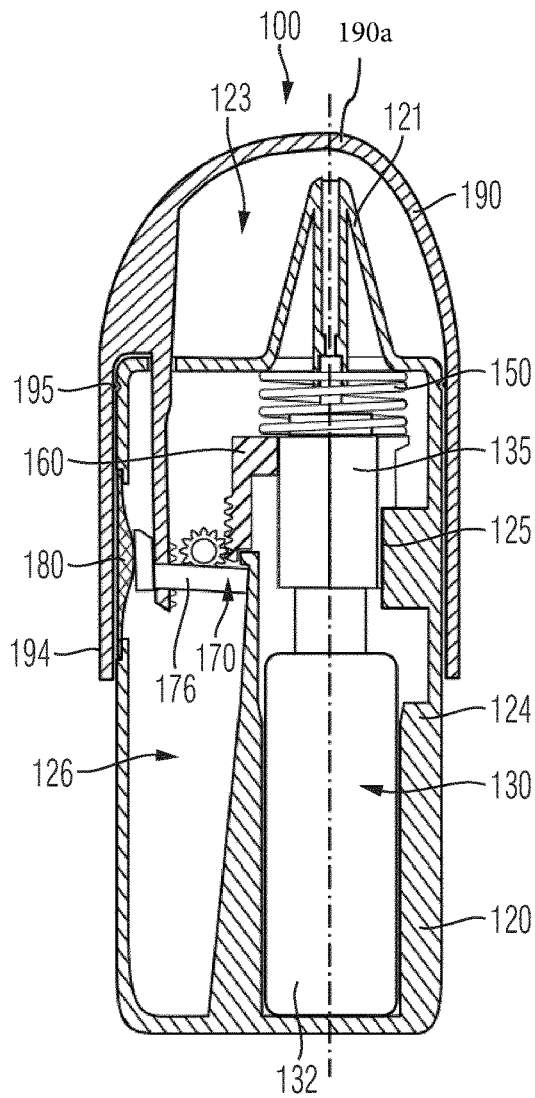
FIG. 20 shows a cross-section through a further fluid dispensing device with the protective cap in the closing position.

The upper end of the housing 120, hence an end face 123 equipped with the orifice 121 is configured to be entirely covered by a detachable protective cap 190. The protective cap 190 comprises a cap portion 190a that is configured to cover and set or to obstruct the orifice 121 of the prior delivery device 130 when the protective cap 190 is in the closing position. The cap 190 can be held in a closing position as illustrated in FIG. 20 by mutually corresponding fastening features 195 and 196 of the protective cap 190 and of the housing 120, respectively. The fastening features and counter-fastening features 195, 196 comprise one of a protrusion and a recess e.g. to provide a snap fit engagement of the protective cap 190 and the housing 120.

As illustrated in FIGS. 20-23 the moveable part 135 of the spray delivery device 130 is connected and fixed to the mechanical coupler 160. The mechanical coupler 160 is slidably displaceable inside the housing 120 by means of a guiding structure 125. The mechanical coupler 160 is in engagement with the biasing member 150. One end 151 of the biasing member 150 is in abutment with an inside facing portion of the housing 120 and a second end 152 of the biasing member 150 is in engagement or in abutment with the mechanical coupler 160. In this way, the mechanical coupler 160 and hence the moveable part 135 attached thereto can be displaced relative to the housing 120 against the action of the biasing member 150.

In an initial configuration as illustrated in FIG. 20 the mechanical coupler is in a preload position. It is kept in the preload position by an activated interlock 170. The interlock 170 comprises a resilient member 173, e.g., in form of a deformable leg 174 attached to or integrally formed with the housing 120. The leg 174 is provided with a catch feature 171 to engage with a snap feature 172 of the mechanical coupler 160. In this way, the mechanical coupler 160 is hindered to move towards the bottom of the housing 120 under the effect of the relaxing biasing member 150. Also here, the biasing member 150 is implemented as a helically wound compression spring.

The trigger 180 is integrated or is mounted flush with a sidewall 124 of the housing 120. It may comprise a resiliently depressible knob or button 182. Inside the housing 120 and hence in the accommodating space 126 there is further provided a bridging piece 176 that provides a mechanical link between the trigger 180 and the leg 174 and hence between the trigger 180 and the interlock 170. The bridging piece 176 may also belong to the trigger 180 or may be integrally formed with the trigger 180. The bridging piece 176 comprises one end in engagement or abutment with an inside portion of the trigger 180. The bridging piece 176 comprises an opposite second end that is in abutment or in engagement with the leg 174 or with a resilient member 173 of the interlock 170.

Figure 21:
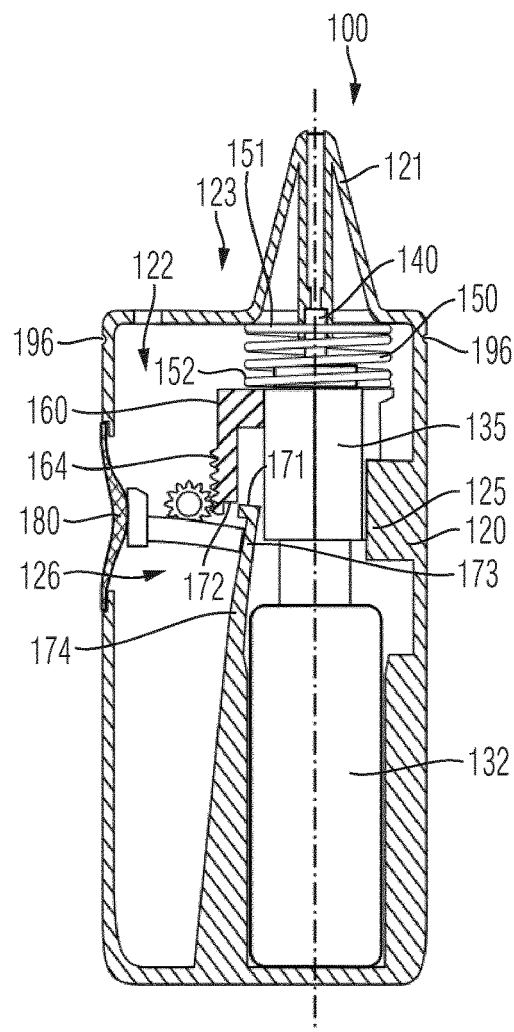
FIG. 21 shows the fluid dispensing device of FIG. 20 with the protective cap removed during or after activation of a trigger.
Figure 22:
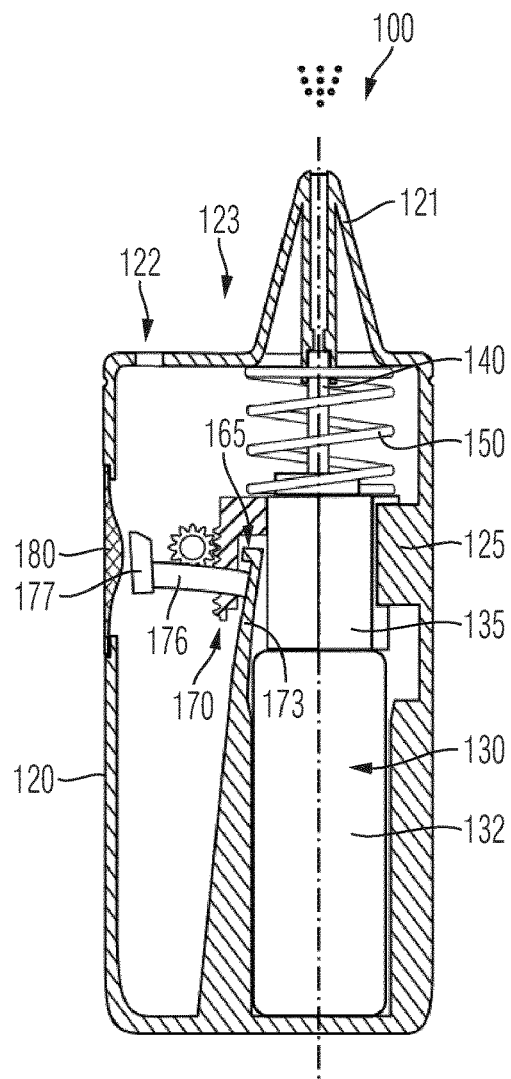
FIG. 22 shows the device of FIG. 20 during or after a dispensing operation and FIG. 23 shows the device of FIGS. 20-22 during the process of reattaching the cap to the housing.

As illustrated in FIG. 21 and as the trigger 180 is depressed the respective motion is transferred via the bridging piece 176 onto the resilient member 173 thus leading to a releasing motion of the catch feature 171 relative to the snap feature 172. As a consequence, the mechanical coupler 160 previously blocked by the interlock 170 is now allowed to move towards the container 132 under the action of the relaxing biasing member 150 as illustrated in FIG. 22. Since the mechanical coupler 160 is connected to and fixed to the moveable part 135 a dispensing operation is conducted and a portion of the fluid is expelled through the outlet 140 and through the orifice 121 as illustrated in FIG. 22.

Figure 23:
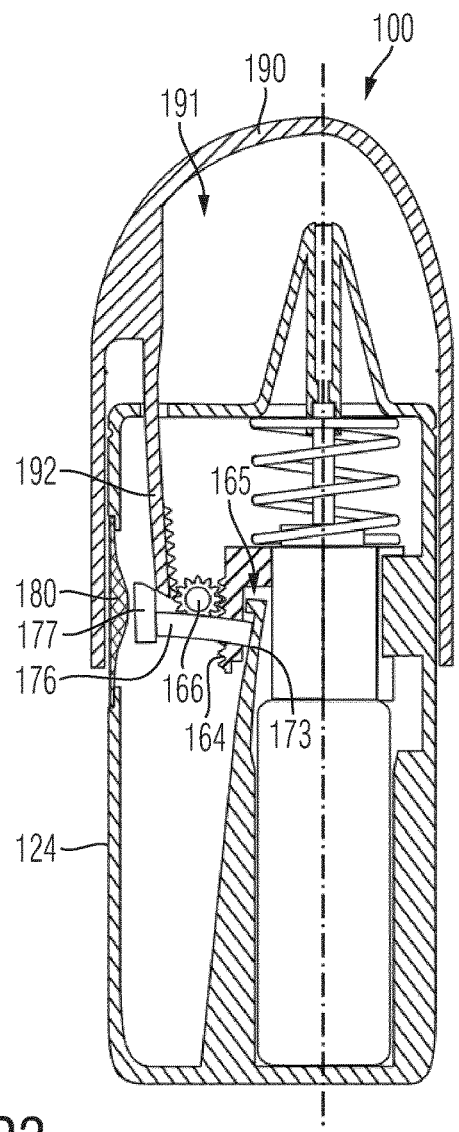

Now, for biasing the biasing member and for transferring the biasing member 150 into the pre-loaded state as illustrated in FIG. 20 the protective cap 190 has to be reassembled onto the housing 20. As described before the protective cap 190 comprises a cup-shaped hollow interior 191. The protective cap 190 further comprises a longitudinal extension 192. As illustrated in FIG. 23 the extension 192 is provided with a rack portion 168, hence with numerous teeth facing towards the mechanical coupler 160. The mechanical coupler 160 is provided with a corresponding rack portion 164 facing towards the sidewall 124 and hence facing towards the trigger 180. Between the rack portions 164, 168 there is provided a pinion 166 rotatably mounted in the housing 120.

In the configurations as illustrated in FIGS. 22 and 23 the free end of the resilient member 173 has entered a receptacle 165 of the mechanical coupler 160 and is hence hindered to relax back into the initial configuration as illustrated in FIG. 20. Here, the resilient member 173 is in engagement with a sidewall of the receptacle 165. In order to provide a resilient return movement of the resilient member 173 the mechanical coupler 160 has to be displaced back into the preload position as illustrated in FIG. 20. The catching and a longitudinal guiding of the free end of the resilient member 173 and the leg 174 in the receptacle 165 is accompanied by a respective displacement of the bridging piece 176. Hence, even when the trigger 180 has been released, the bridging piece 176 rests in the depressed position because it is fixed to the resilient member 173.

The bridging piece 176 may be further provided with a guiding structure 177 effective to keep the rack portion 168 of the longitudinal extension 192 in engagement with the pinion 66. The further rack portion 164 of the mechanical coupler 160 is permanently engaged with the pinion 166. As the protective cap 190 is now pushed into the closing position when starting from the configuration as illustrated in FIG. 23 the rack portion 168 of the longitudinal extension 192 is kept in engagement with the pinion 166. As the protective cap 190 is moved closer to the closing position as illustrated in FIG. 20 the pinion 166 starts to rotate, thus transferring a respective counter-directed motion onto the rack portion 164. As the protective cap 190 is moved closer to the bottom of the housing 120 the mechanical coupler 160 is moved further away from the bottom and towards the upper end face 123.

This movement continues until the interlock 170 is activated again and until the catch feature 171 of the resilient member 173 is aligned with a recessed portion of the snap feature 172. As the catch feature 171 and the snap feature 172 are properly aligned, the resilient member 173 is allowed to bend outwardly, thus leading to an engagement of the catch feature 171 with the snap feature 172. Then, the interlock 170 is activated. The mechanical coupler 160 is hindered to move under the action of the biasing member 150. The biasing member is retained in the pre-loaded state as illustrated in FIGS. 20 and 21. Moreover, the lateral or relaxing movement of the resilient member 173 has the further effect that the bridging piece 176 gets in abutment with an inside of the trigger 180 as illustrated in FIG. 20. The longitudinal extension 192 that was bent towards the pinion 176 by the guiding structure 177 of the bridging piece 176 also relaxes into an initial state according to which the rack portion 168 of the longitudinal extension 192 disengages from the pinion 166.

Also here and as it is apparent from FIG. 20, the sidewall 194 of the protection cap 190 completely covers the trigger 180 and thus impedes and effectively blocks any actuation of the trigger 180 as long as the protective cap 190 is in the closing position.

Figure 24:
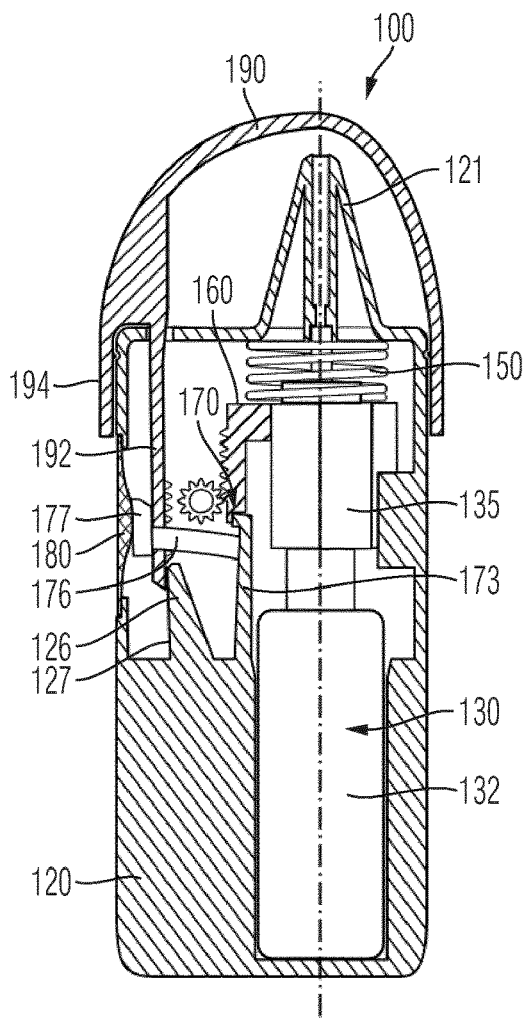
FIG. 24 shows a further example of a fluid dispensing device with a protective cap mounted thereon.

A further example of the fluid dispensing device 100 as illustrated in the sequence of FIGS. 24-27 is quite similar to the example as illustrated before in FIGS. 20-23. Here and contrary to the previous example, the sidewall 194 of the protective cap 190 is somewhat shorter such that the trigger 180 is always accessible, even when the protective cap 190 is in the closing position as illustrated in FIG. 24. In this initial configuration the interlock 170 is activated and blocks a spring-induced displacement of the mechanical coupler 160.

The functionality of the fluid dispensing device 100 as illustrated in FIGS. 24-27 is equivalent or identical to the one as described before in connection with FIGS. 20-23. Insofar, reference is made to the previous example. In order to prevent an uncontrolled, premature or inadvertent release of the interlock 170 the protective cap 190 is effective to block the interlock 170 as long as the protective cap 190 is in the closing position. For this, the housing 120 comprises a further support 126 with a longitudinally extending support face 127. The support face faces towards the interior of the trigger 180. It is located close to the trigger 180 and slightly below or in close vicinity to the bridging piece 176. The support face 127 extends in longitudinal direction and hence substantially parallel to the extension of the longitudinal extension 192.

The distance between the support face 127 and the inside of the trigger 180 in a direction perpendicular to the moving direction of the protective cap 90 and hence perpendicular to the moving direction of the longitudinal extension 92 substantially equals the thickness of the guiding structure 177 and the respective thickness of the longitudinal extension 192. As illustrated in FIG. 24 and when the protective cap 190 is in the closing position the side section of the longitudinal extension 192 facing away from the trigger 180 is in sliding engagement or in abutment with the support face 127.

Figure 25:
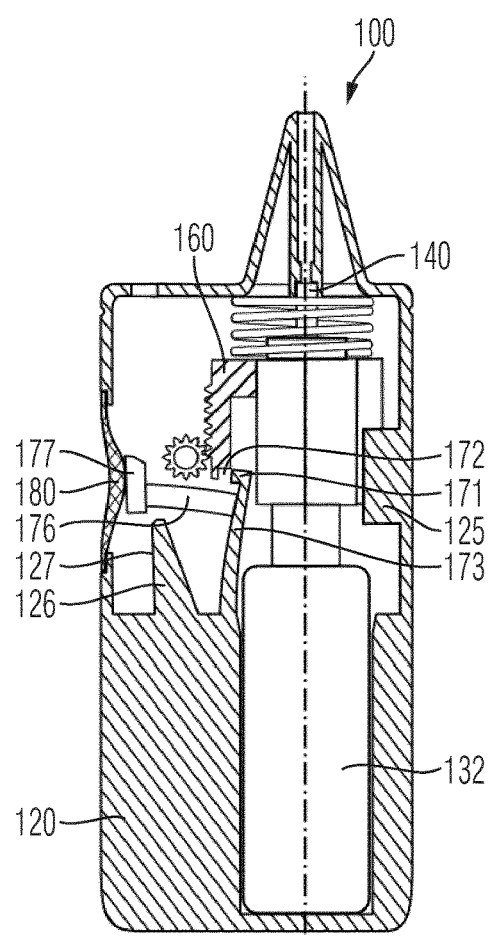
FIG. 25 is illustrative of the device of FIG. 24 after the protective cap has been removed and when a trigger is depressed.
Figure 26:
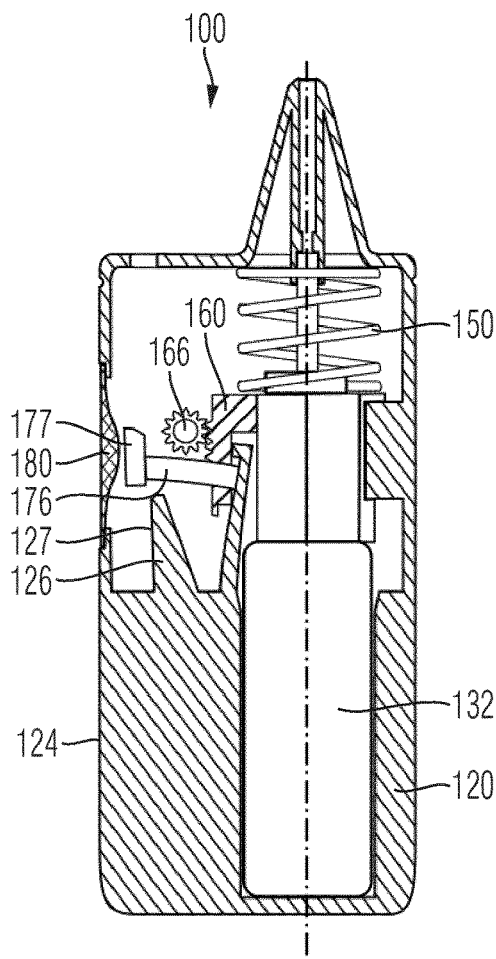
FIG. 26 shows the device of FIG. 25 after or during a dispensing action has taken place and FIG. 27 shows the device of FIG. 26 before or during reattachment of the protective cap.

The longitudinal extension 192 is thus hindered to flex inwardly away from the trigger 180 when the protective cap 190 is in the closing position. The guiding structure 177 of the bridging piece 176 is in abutment with a side section of the longitudinal extension 192 that faces towards the trigger 180. Consequently, a depression of the trigger 180 is blocked. Moreover, due to the abutment and engagement of the longitudinal extension 192 with the support 126 and the support face 127 an inwardly directed movement of the bridging piece 176 and hence of the resilient member 173 is blocked as long as the longitudinal extension 192 is located between the trigger 180 and the support 126 the interlock 170 is locked and cannot be released, e.g., through a depression of the trigger. For this, it is required that the protective cap 190 is transferred into the opening position as illustrated in FIGS. 25 and 26.

Figure 27:
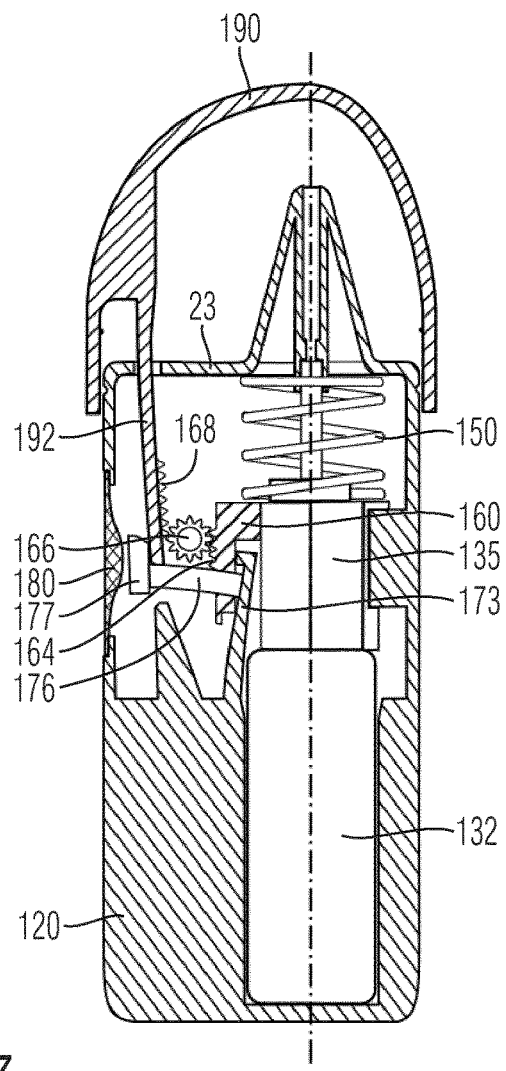

As the protective cap 190 returns into the closing position as illustrated in FIG. 27, the rack portion 164 of the longitudinal extension 192 engages with the pinion 166 and thus induces a biasing or pre-loading displacement of the mechanical coupler 160 and of the biasing member 150 as described before in connection with FIG. 23.

Figure 28:
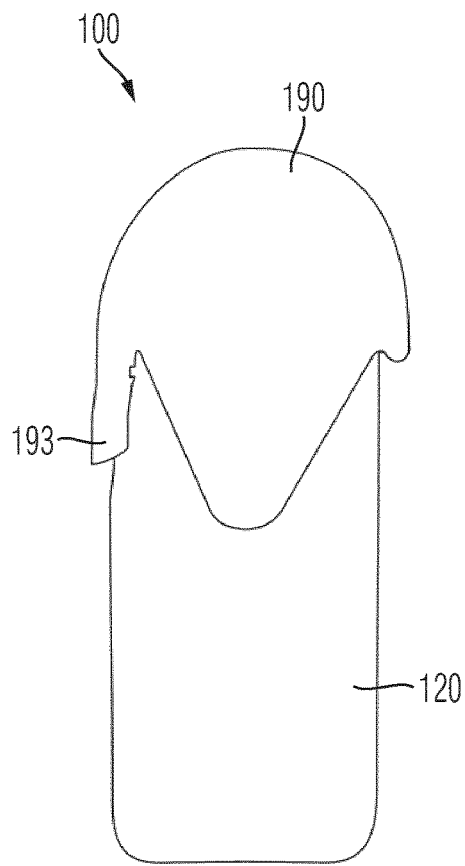
FIG. 28 shows a side view of another example of a fluid dispensing device.
Figure 29:
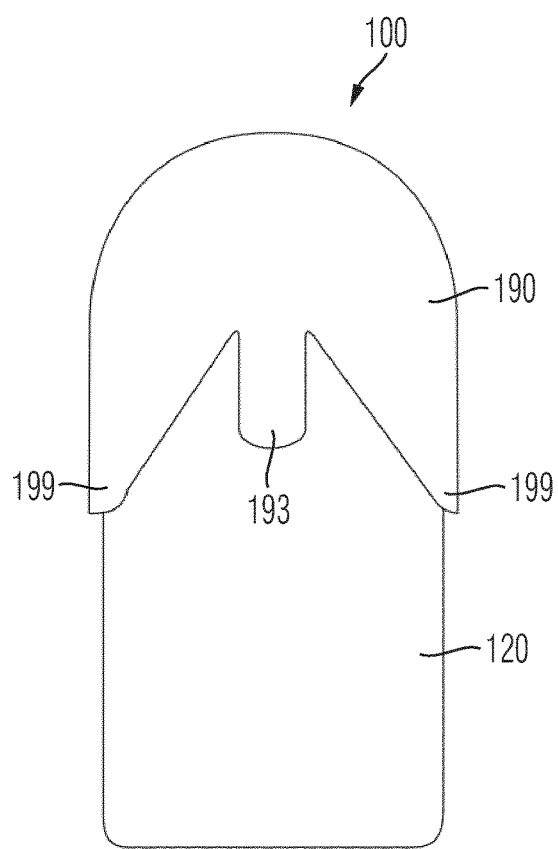
FIG. 29 shows another side view of the fluid dispensing device of FIG. 28 rotated by 90° with the longitudinal axis as an axis of rotation.

In FIGS. 28-34 a further example of a fluid dispensing device 100 is illustrated. In FIG. 28 the fluid dispensing device is shown from the side and in FIG. 29 it is shown in an orientation rotated by 90° with regard to its longitudinal axis. FIG. 29 represents a front view, wherein the protective cap 190 is pivotally attached to the housing 120.

Figure 30:
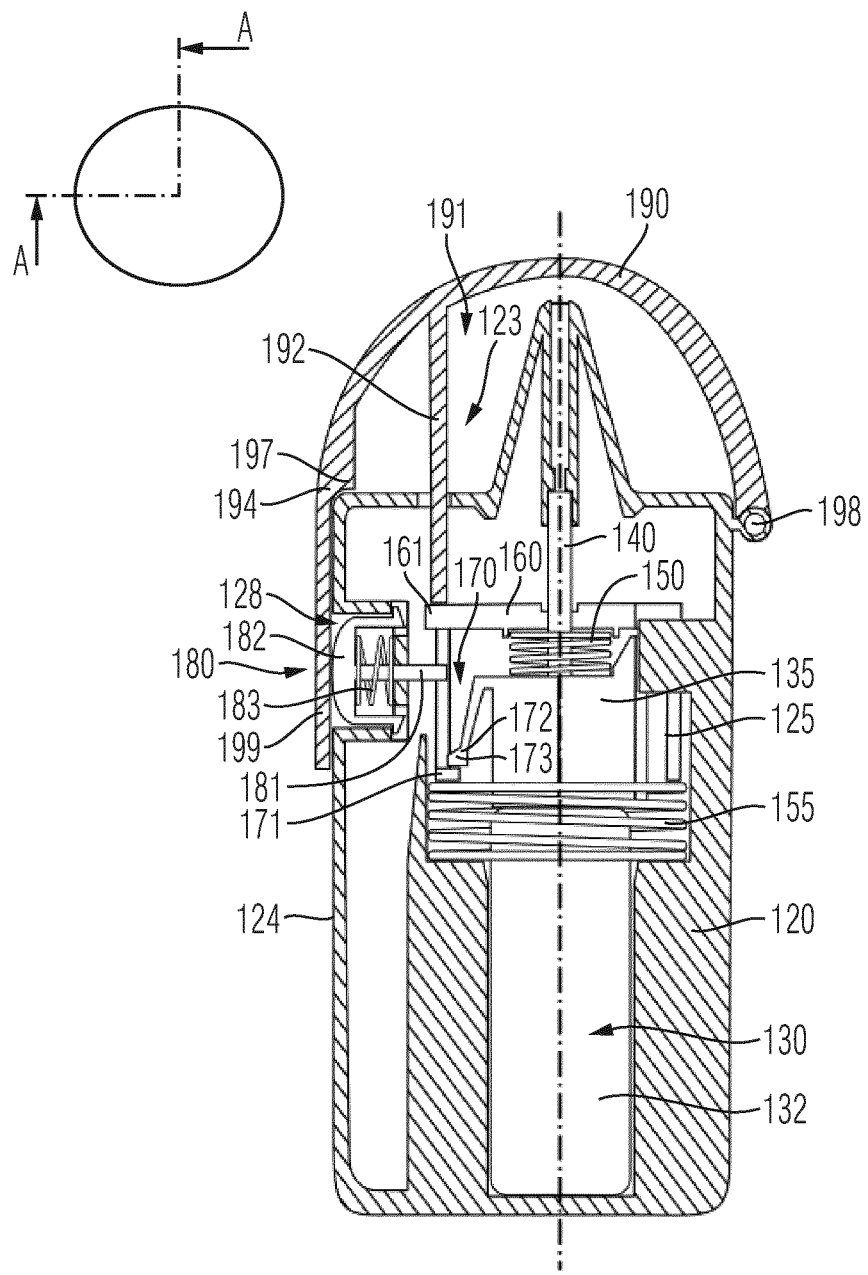
FIG. 30 is illustrative of a particular cross-section A-A through the device of FIGS. 28 and 29 with the protective cap in the closing position.

The cross-sections of FIG. 30 represent a cross-section along the L-shaped line as illustrated in the upper left corner of FIG. 30. The protective cap 190 is pivotally attached to the housing 120 and is pivotable with regard to a pivot axis 198. The protective cap 190 comprises a hollow interior 191. From the top of the cap and inwardly inside the protective cap 190 there extends an elongated protrusion 192. As described before, the elongated protrusion 192 is configured and operable to enter and to penetrate a slit-shaped through opening 122 provided in an upper end face 123 of the housing 120.

The protective cap 190 may be further provided with a handle section 193 located between extensions 199 of the sidewall 194 of the protective cap 190. In the closing position as illustrated in FIG. 30 the extensions 199 effectively cover at least one trigger 180. The trigger 180 comprises an elongated pin 181 extending into the interior of the housing 120. The trigger 180 further comprises a button 182 spring biased by a spring 183 in a receptacle 128 provided in the sidewall 124 of the housing 120.

Figure 33:
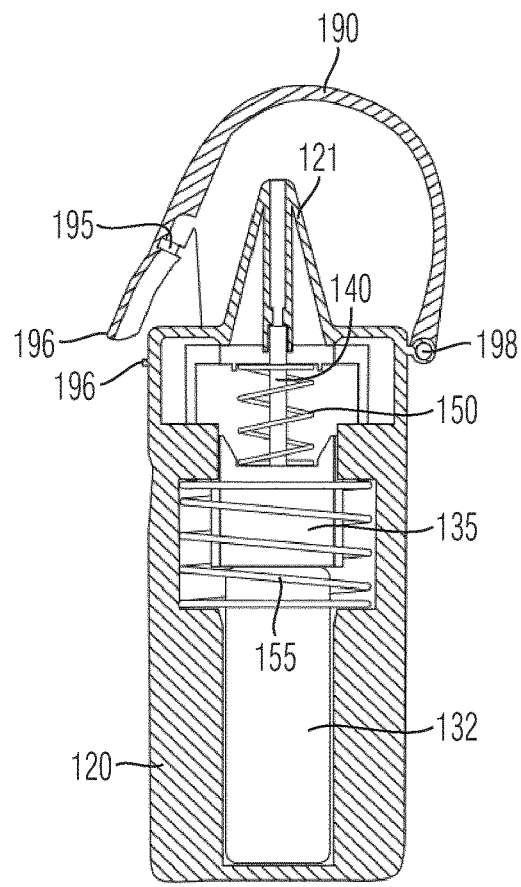
FIG. 33 is illustrative of the process of closing the protective cap as seen from one side of the dispensing device and FIG. 34 shows the configuration of FIG. 33 in another side view.

In the closing position, the handle 193 may snap fit with the housing 120 as indicated in FIG. 33. Here, an inside of the protective cap 190 is provided with a fastening feature 195 configured to engage with a corresponding counter-fastening feature 196 provided on the outside of the housing 120.

In addition and in order to limit a closing movement of the protective cap 190, there is provided an inwardly extending protruding abutment 197 that is configured to engage with the end face 123 of the housing 120, in particular with a corner section of the end face 123.

Figure 31:
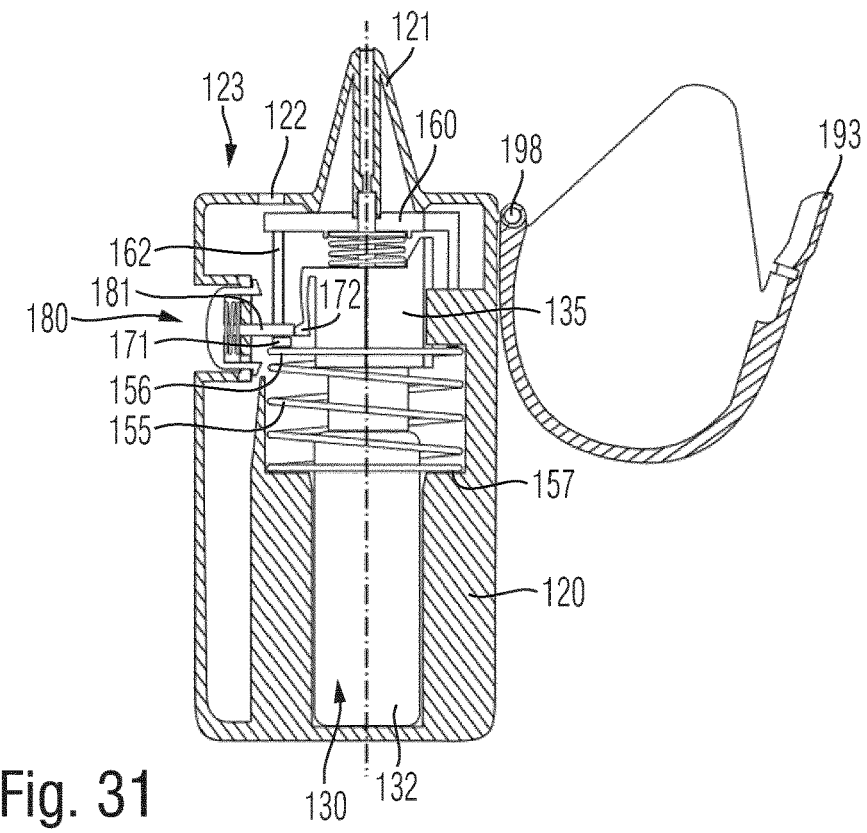
FIG. 31 is illustrative of the device of FIG. 30 with the cap in the opening position and actuation of a trigger.

In the present example the biasing member 150 is located between the mechanical coupler 160 and the moveable part 135 of the spray delivery device 130. The container 132 of the spray delivery device 130 is fixedly attached inside the housing 120. There is further provided an auxiliary spring 155 that is in engagement with the housing 120 and the mechanical coupler 160. A first end 156 of the auxiliary spring 155 is in abutment with an extension 162 of the mechanical coupler 160 as best illustrated in FIG. 31. At an end facing away from the rather planar-shaped or disc-shaped mechanical coupler 160 of the extension 162 there is provided and arranged the catch feature 171 of the interlock 170. The complementary-shaped snap feature 172 is provided at a free end of a resilient member 173 connected to or integrally formed with the moveable part 135 of the spray delivery device 130.

Similar to examples as described above the longitudinal extension 192 is effective to apply a displacement force onto an abutment 161 of the mechanical coupler 160 so as to activate an interlock 170. Here, the interlock is formed between the mechanical coupler 160 and the moveable part 135 of the spray delivery device 130. As illustrated in FIG.

30, there is a mutual engagement or abutment between the catch feature 171 of the mechanical coupler 160 and the snap feature 172 of the moveable part 135 of the spray delivery device 130.

Figure 32:
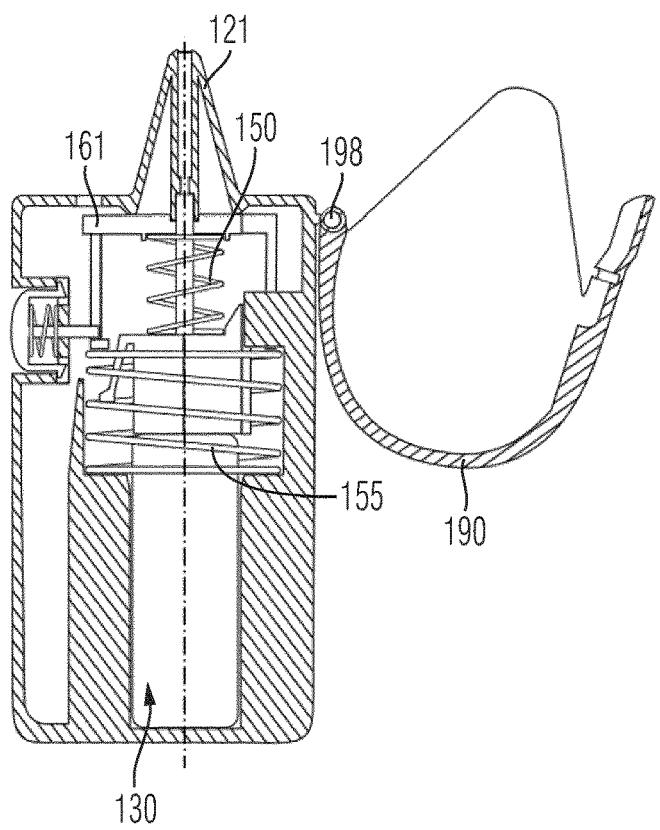
FIG. 32 shows the dispensing device of FIG. 31 after or during dispensing of a dose of the fluid.

The mutually corresponding fastening and counter-fastening features 195, 196 keep the protective cap 190 in the closing position and serve to retain the auxiliary spring 155 in the biased state as illustrated in FIG. 30. As the protective cap 190 is pivoted into the opening position as illustrated in FIGS. 31 and 32 there is no further downwardly acting force present on the mechanical coupler 160. Insofar, the auxiliary spring 155 is operable to displace the assembly of the mechanical coupler 160 and the moveable part 135 away from the container 132. The biasing member 150 is kept in the pre-loaded state during this translational movement because both the moveable part 135 and the mechanical coupler 160 are subject to a common displacement relative to the housing 120 as induced by the auxiliary spring 155.

This movement as induced by the auxiliary spring 155 brings the snap feature 172 in alignment with the pin 181 of the trigger 180. As the trigger 180 is then depressed the snap feature 172 disengages from the catch feature 171. The mechanical coupler 160 is kept in engagement with the upper end or with the end face 123 of the housing 120 by the auxiliary spring 155. Upon release of the interlock 170 the moveable part 135 will then become subject to a movement relative to the housing 120 and relative to the mechanical coupler 160 because of the relaxing motion of the biasing member 150. Consequently, the moveable part 135 is moved towards the container 132 and a predefined amount of the fluid or medicament will be expelled through the orifice 121 as illustrated in FIG. 32.

As the lid or protective cap 190 is closed again the longitudinal extension 192 enters the slit-shaped through opening 122 in the end face 123 of the housing 120. There, the longitudinal extension 192 gets in engagement with the abutment section 161 of the mechanical coupler 160. Consequently, the mechanical coupler 160 is displaced towards the container 130 until the interlock 170 is engaged again and until the auxiliary spring 155 reaches a pre-loaded state as illustrated in FIG. 30.

Figure 34:
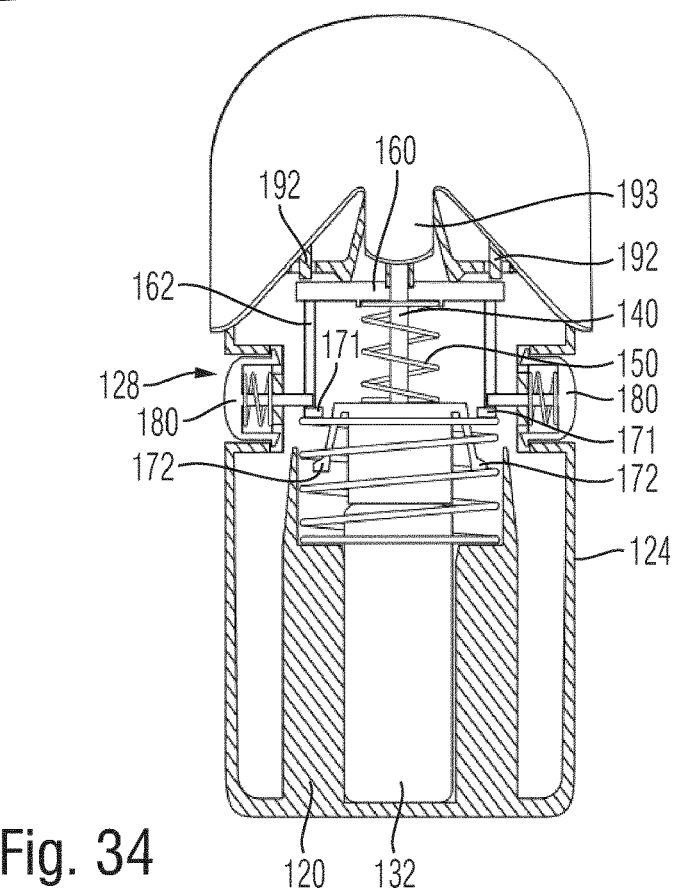

In the cross-section of FIG. 34 it is apparent, that the mechanical coupler 160 and the moveable part 135 each comprise two diametrically opposed mutually corresponding snap features 172 and catch features 171, respectively. Moreover, the fluid dispensing device 100 comprises two triggers 180. In this way, any forces for pre-loading of the biasing member 150, the auxiliary spring 155 as well as any forces for disengaging the interlock 170 can be symmetrically distributed and introduced into the respective components of the fluid dispensing device 100. In FIG. 34 it is further shown that the protective cap 190 also comprises two longitudinal extensions 192 in order to apply a biasing force onto the mechanical coupler 160 rather symmetrically.

Also here and as long as the protective cap 190 is in the closing position actuation of the trigger 180 is effectively blocked.

Figure 35:
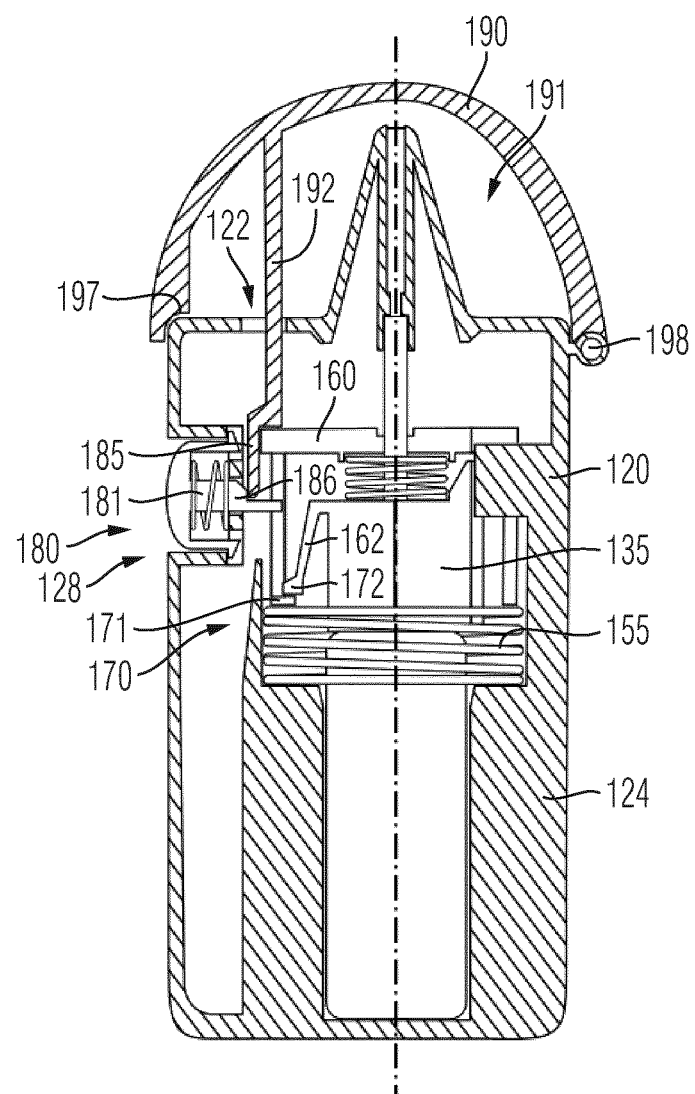
FIG. 35 shows a further example of a dispensing device with a pivotable protective cap in a closing position.
Figure 36:
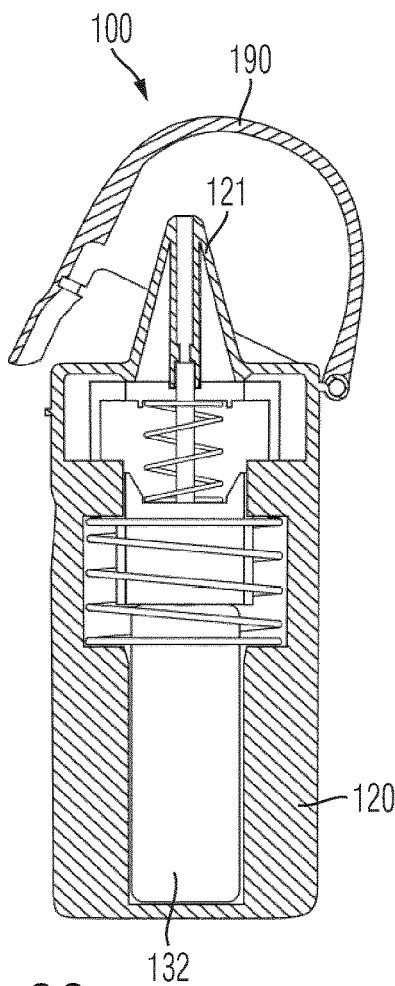
FIG. 36 shows the device of FIG. 35 during a closing operation of the protective cap as seen from one side and FIG. 37 shows the closing operation of FIG. 36 as seen from a front side of the fluid dispensing device.
Figure 37:
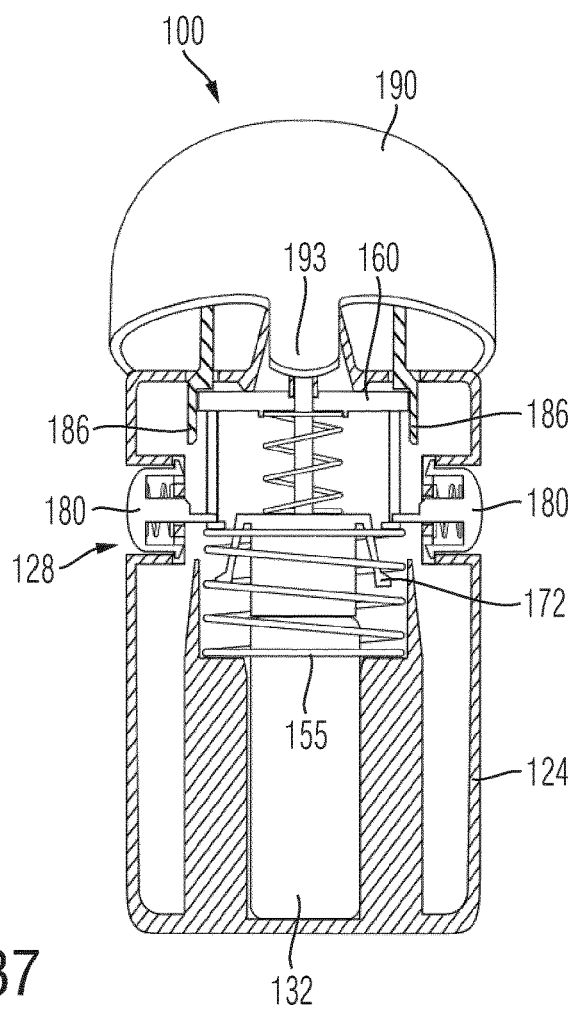

In FIGS. 35-37 a similar example as described with respect to FIGS. 30-34 is illustrated. Here and contrary to the previous example the protective cap 190 is void of an extension 199 operable to cover the trigger 180 when the protective cap 190 is in the closing position. In order to prevent an uncontrolled, premature or inadvertent release of the interlock the longitudinal extension 192 of the protective cap 190 comprises a lateral abutment feature 185 that enters a free space between the mechanical coupler 160 and an inside of the trigger 180. In particular, the pin 181 comprises a recessed portion 186 to engage with the lateral abutment feature 185 as the protective cap 190 arrives in the closing position. When the lateral abutment feature 185 engages the pin 181 and hence the recessed portion 186 thereof, a depression of the trigger is effectively blocked and prevented. Apart from that, in the closing position of the protective cap 190, the interlock 170 as provided by the mutually engaged catch feature 171 and the correspondingly-shaped snap feature 172 is located at a certain distance from the trigger 180. So as long as the interlock 170 is offset from the trigger 180 depression of the trigger 180 will be ineffective to release the interlock 170. It is only upon opening of the protective cap 190 that the auxiliary spring 155 induces a sliding motion onto the interlock 170 such that the interlock 170 aligns with and operably engages with the trigger 180.

The trigger as described and illustrated with the examples of FIGS. 28-35 is equally implementable with any of the examples of FIG. 1-27 and vice versa, also the trigger or trigger assemblies 80 as illustrated in FIGS. 2-27 may equally apply to the examples of FIGS. 28-35.

The further example of the fluid dispensing device as illustrated in FIGS. 44-51 has some similarities to the example as described above in connection with FIGS. 8-13. In particular, reference numerals used above with respect to the examples of FIGS. 1-19 and as used in FIGS. 44-51 refer to the same or like components of the fluid dispensing device. Insofar the description of FIGS. 1-19 applies to a large extent also to the examples as shown in FIGS. 44-51.

The fluid dispensing device 10 as described in FIGS. 44-51 comprises a housing 20 with a sidewall 24. The housing may be of elongated, e.g., somewhat cylindrical shape but does not have to be cylindrically shaped. On an upper end of the housing 20 there is provided an orifice 21 in flow connection with an outlet 40 of a spray delivery device 30.

The spray delivery device 30 is mounted on or in a mechanical coupler 60. The mechanical coupler 60 may comprise a tubular-shaped barrel accommodating the spray delivery device 30, e.g., a container 32 of the spray delivery device. The mechanical coupler 60 may comprise a hollow sleeve 64 or barrel in which the spray delivery device 30 may be fixed. The spray delivery device 30 may be frictionally engaged with the sleeve 64 of the coupling member 60.

As described above, the coupling member 60 is biased by the mechanical biasing member 50. The first end 51 of the mechanical biasing member 50 is in abutment with a flange section 66 protruding outwardly from the sidewall of the sleeve 64. An opposite second end 52 is in abutment with an inside facing portion of the housing 20. In particular, the second end 52 of the biasing member 50 is in abutment with a bottom of the housing 20. The biasing member 50 is arranged around a tubular-shaped guiding structure 25. The guiding structure may comprise or constitute an outer sleeve configured to receive the sleeve 64 as an inner sleeve. Hence, the outer sleeve of the guiding structure 25 provides a longitudinal guiding of the mechanical coupler 60.

Figure 47:
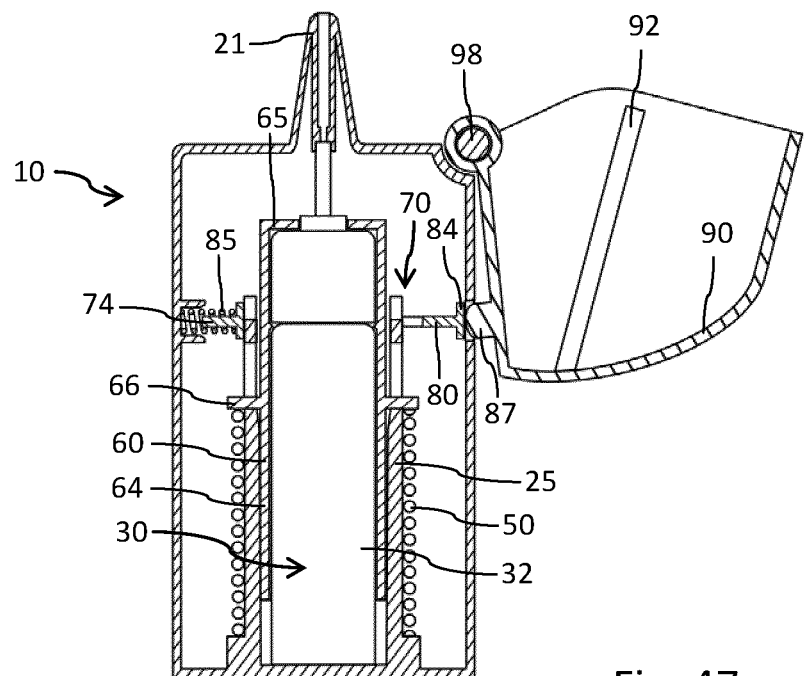
FIG. 47 is a further illustration in accordance to FIG. 44 with the protective cap in the opening position.
Figure 48:
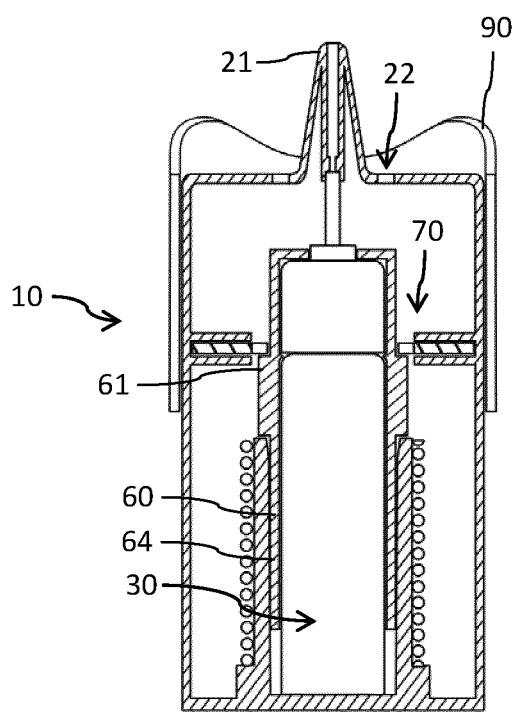
FIG. 48 shows the device of FIG. 47 along the cross-section of FIG. 45.
Figure 49:
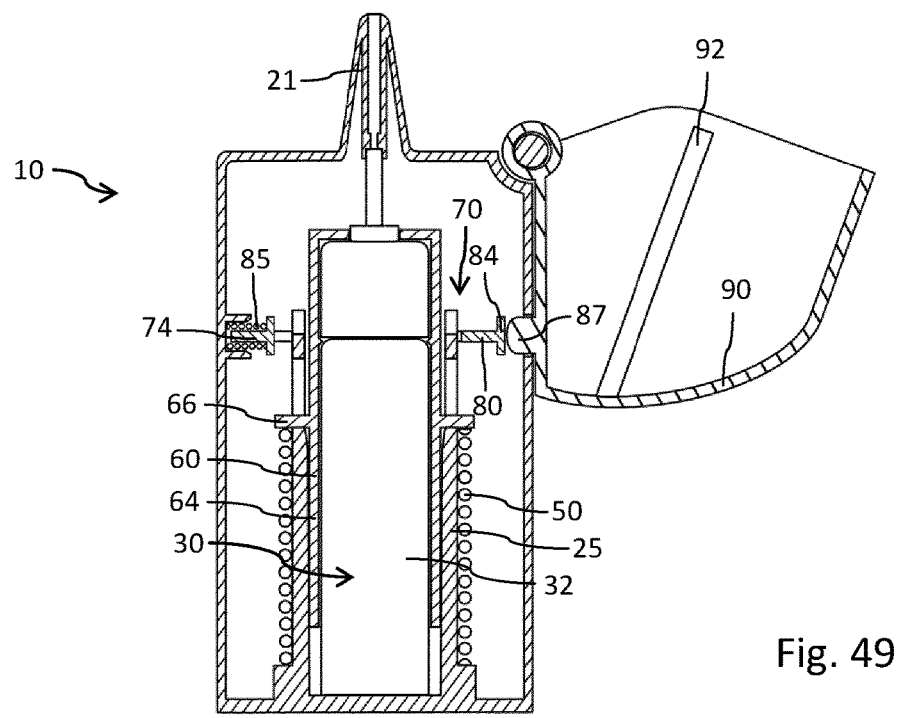
FIG. 49 shows the device of FIG. 47 when the protective cap depresses the trigger.
Figure 50:
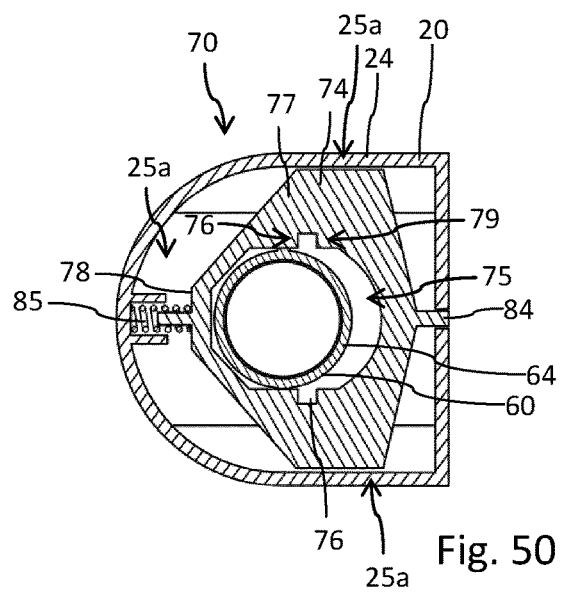
FIG. 50 shows a cross-section through the interlock of FIG. 44 before depression of the trigger.
Figure 51:
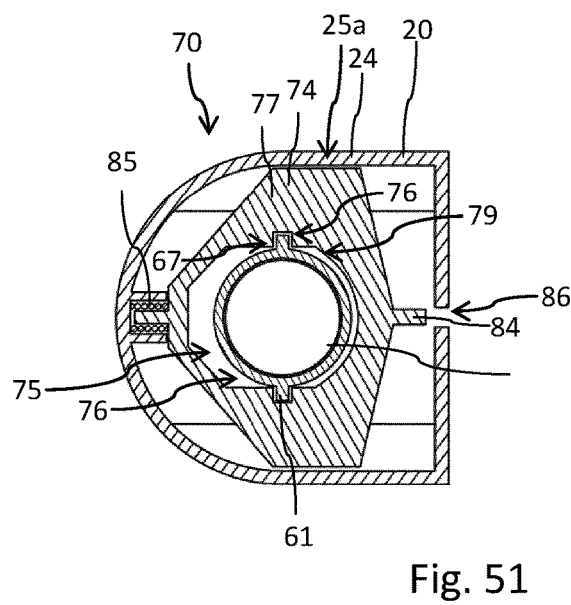
FIG. 51 shows a further cross-section through the interlock of FIG. 44 during or after depression of the trigger.

The mechanical coupler 60 is held and fixed in the preload position by the interlock 70. The interlock 70 is displaceable or reconfigurable from an interlock position or interlocked configuration as shown in FIGS. 44, 45, 50 and 52 into a release position or release configuration as illustrated in FIGS. 49, 51 and 53. For transferring the interlock 70 into the release configuration the protective cap 90 has to approach an opening position or opening configuration as illustrated in FIGS. 47 and 49.

The interlock 70 is further operationally engaged with the trigger 80. The trigger 80 is located inside a recess 86 or recessed portion of the sidewall 24 of the housing 20. The trigger 80 comprises a trigger button 84 entirely located inside the recess 86. The trigger button 84 does not protrude from the recess 86. A depressible or user-actuatable portion of the button 84 is located at a well-defined non-zero distance from the outside surface of the sidewall 24 of the housing 20. This applies when the interlock 70 is in the interlock configuration or interlock position. In this way and as illustrated for instance in FIG. 44, the interlock 70 and/or the trigger 80 cannot be actuated by a finger of a user because the recess 86 has a diameter or cross-section that is smaller than the respective cross-section of a human finger.

Hence, for activating or for depressing of the trigger 80 it is necessary to insert a tool into the recess 86 of the housing 20. Here, and since the protective cap 90 is pivoted mounted to the housing 20 with regards to a pivot axis 98 the protective cap 90 is equipped with a respective tool, e.g. in form of a protrusion 87, to enter the recess 86 and to depress the button 84 of the trigger 80.

The protective cap 90 comprises a protrusion 87 extending outwardly from an outside surface of the protective cap 90. Typically, and as becomes apparent from a comparison of FIGS. 44 and 47 the radial distance between the protrusion 87 and the pivot axis 98 is identical or corresponds to the radial distance between the recess 86 and the pivot axis 98. When the protective cap 80 has been pivoted to approach the final opening position as illustrated in FIG. 47 the protrusion 87 has already entered the recess 86 and is in abutment with the depressible button 84 of the trigger 80. Then, a user may invoke a further pivoting motion of the protective cap 90 towards a final opening position such that the protrusion 87 further enters the recess 86, thereby depressing the button 84 of the trigger 80.

Figure 45:
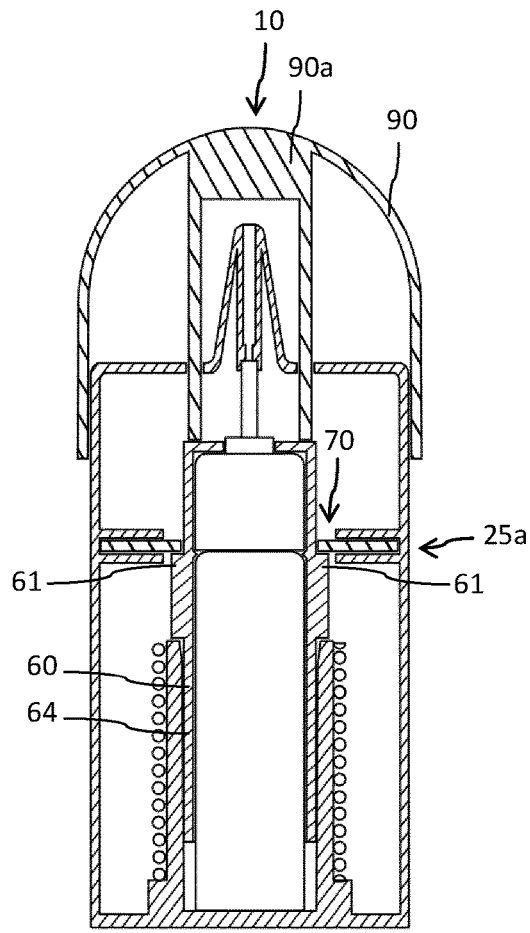
FIG. 45 shows the fluid dispensing device according to FIG. 44 when rotated by 90°.
Figure 46:
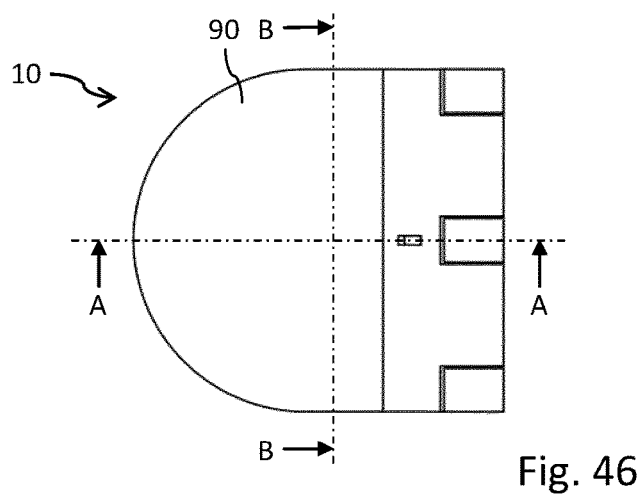
FIG. 46 is a top view of the fluid dispensing device of FIGS. 44 and 45.

Depression of the button 80 leads to a displacement of the interlock 70 along a first direction of movement. The first direction of movement may be perpendicular to the axis of elongation of the mechanical biasing member 50 and/or perpendicular to the longitudinal extension of the sleeve 64 of the mechanical coupler 60. As illustrated in FIGS. 45 and 50 in the interlock configuration the interlock 70 is in engagement with an abutment 61 of the mechanical coupler 60. The abutment 61 is provided as a radially widened shoulder portion being in vertical or axial abutment with the interlock 70.

As becomes apparent from a comparison of FIGS. 50 and 51 the interlock 70 comprises a planar-shaped body 74 with an aperture 75. The aperture 75 is shaped to receive the mechanical coupler 60 there through.

In the interlock configuration as shown in FIG. 50, the aperture 75 is arranged slightly offset from the cross-section of the mechanical coupler 60 along the first direction of movement. Hence, the radially outwardly protruding abutment 61 of the mechanical coupler 60 is engaged axially or in vertical direction with a lower surface of a side edge of the aperture 75.

The slider 77 is slidably guided by a further guiding structure 25a of the housing 20. It may be guided along the first direction of movement as it is apparent from a comparison of FIGS. 50 and 51. The movement of the slider 76 is typically triggered by a respective depression of the button 84. The button 84 and hence the trigger 80 may be integrally formed with the interlock 70. The button 84 may be an integral component of the body 74. The aperture 75 of the slider 77 comprises a shape and/or a mechanical code or a keyed structure 79 that matched with a mechanical code or keyed structure 67 provided on the outside circumference of the mechanical coupler 60.

The keyed structure 79 and/or a side edge of the aperture 75 may comprise at least one recess 76 configured to receive a correspondingly shaped protrusion, e.g., in form of the radially outwardly protruding abutment 61 of the mechanical coupler 60. With other examples, the keyed structure 67 of the mechanical coupler 60 comprises at least one recess configured to engage or to receive a recess of the keyed structure 79 of the aperture 75 or slider 77.

By displacing the interlock 70 into the position or configuration as illustrated in FIG. 51, the mechanical code or the keyed structure 67 of the mechanical coupler 60 comes into alignment with the respective mechanical code or keyed structure 79 of the aperture 75. In this way, the axial or longitudinal abutment between the mechanical coupler 60 and the interlock 70 is abrogated and the mechanical coupler 60 with the spray delivery device 30 mounted therein is allowed to move towards the orifice 21 under the action of the relaxing mechanical biasing member 50.

As described above in connection with FIGS. 1-19 an interior of the protective cap 90 is provided with at least one longitudinal extension 92 configured to reach through a through opening 22 provided in an upper end face 21 of the housing. In this way and when closing the cap 90, the protrusions 90 engage with an upper end wall or end face 65 of the mechanical coupler 60. Then and during a return motion of the protective cap 90 towards and into the closing position as illustrated in FIG. 44 the mechanical coupler 60 and the spray delivery device 30 return into their initial position or configuration.

The trigger-induced movement of the interlock 70 is accompanied by a compression of a return spring 85 as illustrated by a comparison of FIGS. 50 and 51. Here, a compression spring 85 is arranged between an abutment 78 of the body 74 of the interlock 70 and an inside facing surface of the sidewall 24 of the housing 20. Urging or moving the interlock 70 into the release configuration as illustrated in FIG. 51 leads to a biasing of the return spring 85.

As the protective cap 90 returns into the closing position, the protrusion 87 is removed from the recess 86. As long as the keyed structure 67 of the mechanical coupler 60 is engaged with the correspondingly shaped keyed structure 79 of the interlock 78 movement of the interlock 70 towards the interlock position or interlocked configuration is effectively blocked.

Figure 44:
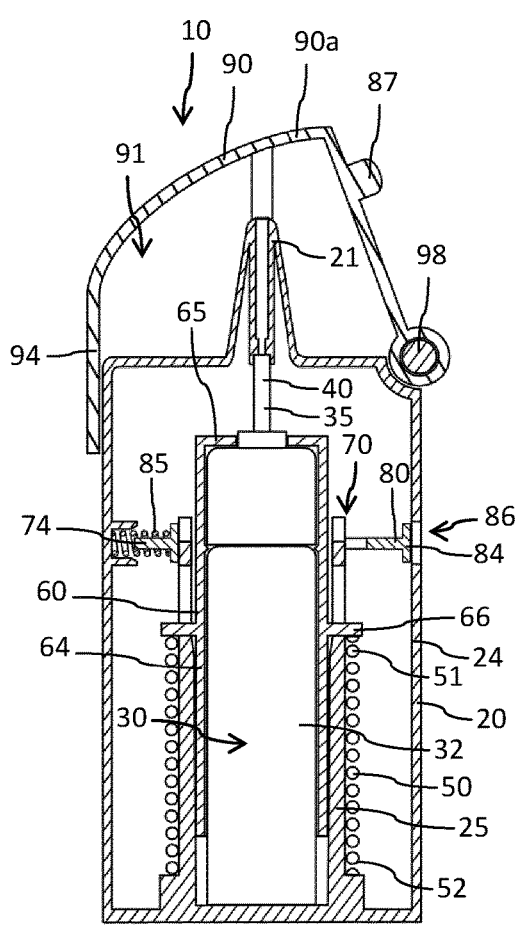
FIG. 44 shows a further example of the fluid dispensing device along a first cross-section.

Now, when reaching the initial configuration as illustrated in FIG. 44, the mechanical coupler 60 and the keyed structure 67 thereof disengage from the keyed structure 79 of the interlock 70. The interlock 70 is then free to become displaced into the interlock position or interlocked configuration as shown in FIG. 50 under the effect of the return spring 85.

Figure 52:
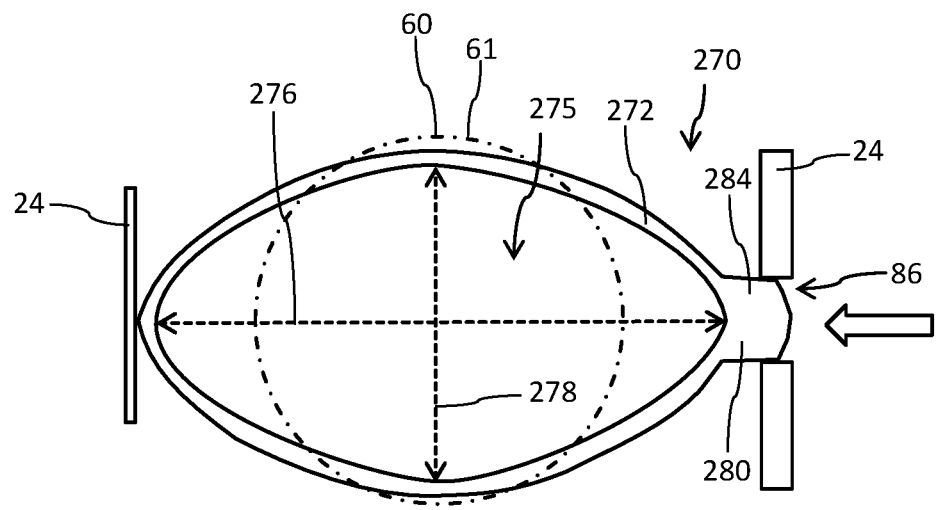
FIG. 52 shows a further example of a resiliently deformable interlock in an initial configuration.
Figure 53:
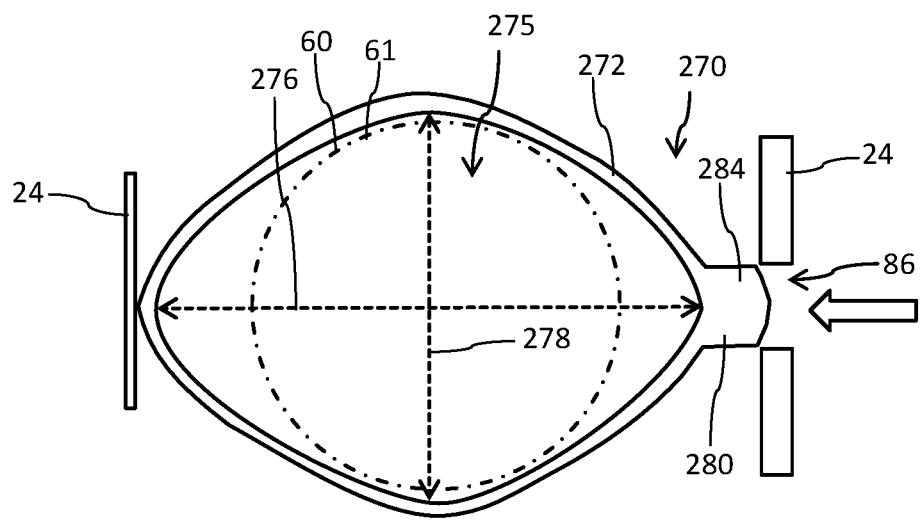
FIG. 53 shows the example of FIG. 52 after or during depression of the trigger.

In the further example as illustrated in FIGS. 52 and 53 the interlock 270 is also integrally formed with a trigger 280. But here, the interlock 270 comprises a resilient ring structure 272. In the initial configuration as illustrated in FIG. 52 the resilient ring structure 272 comprises an oval shape. A long axis 276 of the oval shaped ring structure 272 is larger than a diameter of the mechanical coupler 60 illustrated in dash dotted lines, but a short axis 278 of the ring structure 272 is shorter that the respective dimensions of the mechanical coupler 60.

In an initial configuration such as illustrated in FIG. 44, the aperture 275 of the oval ring structure does not match the outer circumference or outer geometry of the mechanical coupler 60. Hence, the abutment 61 of the mechanical coupler 60, which may be provided by the upper end wall 65, is at least in sections in axial or longitudinal abutment with the oval shaped ring structure 272.

With the examples of FIG. 52 and FIG. 53 the trigger button 284 extends outwardly from the ring structure 272. It is located at an outside section of the ring structure 272. The trigger 280 and the outwardly extending trigger button 284 are provided at a longitudinal end of the long axis of the oval shaped ring structure 272. An opposite end of the long axis is in abutment with the sidewall 24 of the housing 20.

Depression of the trigger 280 radially inwardly leads to a reduction of the length of the long axis 276 at the benefit of an increase of the length of the short axis 278 of the oval shaped ring structure 272. When the deformation of the ring structure 272 is such that the short axis 278 of the ring structure 272 is equal to or exceeds the diameter of the mechanical coupler 60 along the short axis 278 the axial abutment between the interlock 70 and the mechanical coupler 60 is effectively abrogated or canceled. The mechanical coupler 60 is then free to move in longitudinal direction relative to the interlock 270.

| Reference numbers | |
|---|---|
| 10 | fluid dispensing device |
| 20 | housing |
| 21 | orifice |
| 22 | through opening |
| 23 | end face |
| 24 | sidewall |
| 25 | guiding structure |
| 25a | guiding structure |
| 26 | accommodating space |
| 27 | jet nozzler |
| 28 | shaft portion |
| 29 | aperture |
| 30 | spray delivery device |
| 31 | tube |
| 32 | container |
| 33 | inlet valve |
| 35 | moveable part |
| 36 | outlet valve |
| 38 | chamber |
| 40 | outlet |
| 41 | shaft |
| 42 | spring |
| 45 | base |
| 50 | biasing member |
| 51 | first end |
| 52 | second end |
| 60 | mechanical coupler |
| 61 | abutment |
| 62 | strut |
| 63 | corner section |
| 64 | sleeve |
| 65 | end wall |
| 66 | flange section |
| 67 | keyed structure |
| 70 | interlock |
| 71 | catch feature |
| 72 | snap feature |
| 73 | resilient member |
| 74 | body |
| 75 | aperture |
| 76 | recess |
| 77 | slider |
| 78 | abutment |
| 79 | keyed structure |
| 80 | trigger |
| 81 | pin |
| 82 | support structure |
| 83 | bulged portion |
| 84 | button |

-continued

| Reference numbers | |
|---|---|
| 85 | spring |
| 86 | recess |
| 87 | protrusion |
| 90 | protective cap |
| 90 | cap portion |
| 91 | hollow interior |
| 92 | extension |
| 93 | shoe section |
| 94 | sidewall |
| 95 | fastening feature |
| 96 | counter-fastening feature |
| 97 | recessed portion |
| 98 | pivot axis |
| 99 | extension |
| 100 | fluid dispensing device |
| 120 | housing |
| 121 | orifice |
| 122 | through opening |
| 123 | end face |
| 124 | sidewall |
| 125 | guiding structure |
| 126 | support |
| 127 | support face |
| 128 | receptacle |
| 130 | spray delivery device |
| 131 | tube |
| 132 | container |
| 133 | inlet valve |
| 135 | moveable part |
| 136 | outlet valve |
| 138 | chamber |
| 140 | outlet |
| 141 | shaft |
| 142 | spring |
| 145 | base |
| 146 | shaft |
| 150 | biasing member |
| 151 | first end |
| 152 | second end |
| 155 | auxiliary spring |
| 156 | first end |
| 157 | second end |
| 160 | mechanical coupler |
| 161 | abutment |
| 162 | extension |
| 164 | rack portion |
| 165 | receptacle |
| 166 | pinion |
| 168 | rack portion |
| 170 | interlock |
| 171 | catch feature |
| 172 | snap feature |
| 173 | resilient member |
| 174 | leg |
| 176 | bridging piece |
| 177 | guiding structure |
| 180 | trigger |
| 181 | pin |
| 182 | button |
| 183 | spring |
| 185 | lateral abutment feature |
| 186 | recessed portion |
| 190 | protective cap |
| 190a | cap portion |
| 191 | hollow interior |
| 192 | extension |
| 193 | handle |
| 194 | sidewall |
| 195 | fastening feature |
| 196 | fastening feature |
| 197 | abutment 198 pivot axis |
| 270 | interlock |
| 272 | ring structure |

-continued

| Reference numbers | |
|---|---|
| 275 | aperture |
| 276 | long axis |
| 278 | short axis |
| 280 | trigger |
| 284 | button |

The invention claimed is:

1. A fluid dispensing device comprising:
a housing, the housing comprising an orifice and wherein the housing is configured to accommodate at least a portion of a spray delivery device comprising an outlet through which a fluid stored in the spray delivery device is dischargeable,
the fluid dispensing device further comprising:
a protective cap defining an interior space configured to accommodate the outlet of the spray delivery device and comprising at least a cap portion, wherein the protective cap is configured for fitting to the housing at least in a closing position relative to the housing, in which the cap portion covers the orifice,
a mechanical spring reversibly transferable between a pre-loaded state and an unloaded state and configured to store mechanical energy in the pre-loaded state effective to produce a spray discharge of the spray delivery device,
a releasable interlock configured to retain the mechanical spring in the pre-loaded state,
a mechanical coupling member engaged with the mechanical spring and displaceable relative to the housing into a preload position against an action of the mechanical spring for transferring the mechanical spring into the pre-loaded state, and
a manually actuatable trigger operationally engaged with the releasable interlock and configured to release the releasable interlock when actuated,
wherein the protective cap is transferable into an opening position relative to the housing and wherein the protective cap is operable to actuate the manually actuatable trigger as the protective cap approaches or reaches the opening position, and
wherein the protective cap is operably engageable with the mechanical coupling member and wherein the protective cap is operable to displace the mechanical coupling member into the preload position against the action of the mechanical spring when approaching the closing position relative to the housing.

2. The fluid dispensing device according to claim 1, wherein the protective cap is at least one of detachably connectable to the housing, pivotally connected to the housing, and slidably connected to the housing.

3. The fluid dispensing device according to claim 1, wherein when in the closing position the protective cap is operable to block a release of the releasable interlock.

4. The fluid dispensing device according to claim 1, wherein the manually actuatable trigger is located in a recessed portion of the housing.

5. The fluid dispensing device according to claim 1, wherein the protective cap comprises a protrusion extending outwardly from an outside surface of the protective cap and configured to engage or to depress the manually actuatable trigger.

6. The fluid dispensing device according to claim 1, wherein the releasable interlock comprises a slider slidably guided along a first direction of movement by a guiding structure of the housing.

7. The fluid dispensing device according to claim 1, wherein the releasable interlock is displaceable from an interlock position into or towards a release position against the action of a return spring.

8. The fluid dispensing device according to claim 1, wherein the housing comprises a longitudinal guiding structure operable to guide the mechanical coupling member and wherein the mechanical coupling member is displaceable between the preload position and an unload position along the longitudinal guiding structure.

9. The fluid dispensing device according to claim 1, wherein the releasable interlock comprises an aperture sized to receive at least one of the mechanical coupling member and the spray delivery device.

10. The fluid dispensing device according to claim 1, wherein the releasable interlock comprises a resiliently deformable oval shaped ring structure.

11. The fluid dispensing device according to claim 1, wherein the protective cap comprises a longitudinal extension extending into or through the interior space, wherein the longitudinal extension is configured to reach through at least one of the orifice or through a through opening in an end face or sidewall of the housing when the protective cap approaches the closing position.

12. The fluid dispensing device of claim 11, wherein the mechanical coupling member comprises an abutment configured to engage with the longitudinal extension of the protective cap.

13. The fluid dispensing device according to claim 1, wherein the spray delivery device or a portion thereof is arranged inside the housing and wherein the outlet of the spray delivery device coincides with the orifice or is arranged in an alignment with the orifice.

14. The fluid dispensing device according to claim 13, wherein the spray delivery device further comprises:
a container providing a reservoir for the fluid,
a movable part displaceable relative to the container between a delivery device preload position and a discharge position.

15. The fluid dispensing device according to claim 14, wherein one of the container and the movable part is engaged with or is attached to one of the mechanical coupling member and the mechanical spring.

16. The fluid dispensing device according to 14, wherein at least one of the outlet and the container is fixed inside the housing and wherein a movable part of the spray delivery device is mechanically engaged with or is connected to one of the mechanical coupling member and the mechanical spring.

17. The fluid dispensing device according to claim 14, wherein the outlet is fixed to the movable part of the spray delivery device and wherein the container of the spray delivery device is mechanically engaged with or is connected to one of the mechanical coupling member and the mechanical spring.

* * * * *